United States Patent
MacPhee et al.

(10) Patent No.: US 9,259,503 B2
(45) Date of Patent: *Feb. 16, 2016

(54) METHODS AND DRESSINGS FOR SEALING INTERNAL INJURIES

(71) Applicant: STB, Ltd., Bellevue, WA (US)

(72) Inventors: Martin MacPhee, Darnestown, MD (US); Jerry Kanellos, Victoria (AU); Belinda Wilmer, Martinsburg, WV (US); Dawson Beall, Gaithersburg, MD (US)

(73) Assignee: STB, LTD., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/829,630

(22) Filed: Aug. 18, 2015

(65) Prior Publication Data

US 2015/0352245 A1 Dec. 10, 2015

Related U.S. Application Data

(63) Continuation of application No. 13/080,086, filed on Apr. 5, 2011, now Pat. No. 9,131,929, which is a continuation of application No. 12/222,277, filed on Aug. 6, 2008, now abandoned.

(60) Provisional application No. 60/935,311, filed on Aug. 6, 2007.

(51) Int. Cl.
| | |
|---|---|
| A61B 17/03 | (2006.01) |
| A61L 15/00 | (2006.01) |
| A61B 17/00 | (2006.01) |
| A61L 15/44 | (2006.01) |
| A61K 38/36 | (2006.01) |
| A61K 38/48 | (2006.01) |

(52) U.S. Cl.
CPC ............... *A61L 15/44* (2013.01); *A61K 38/363* (2013.01); *A61K 38/4833* (2013.01); *A61L 2300/252* (2013.01); *A61L 2300/254* (2013.01); *A61L 2400/04* (2013.01)

(58) Field of Classification Search
CPC .................................................. A61B 17/00491
See application file for complete search history.

(56) References Cited

U.S. PATENT DOCUMENTS

| | | | | |
|---|---|---|---|---|
| 4,442,655 | A * | 4/1984 | Stroetmann | A61K 38/363 106/124.1 |
| 4,453,939 | A * | 6/1984 | Zimmerman | A61L 15/325 602/50 |
| 6,113,948 | A * | 9/2000 | Heath | A61K 9/1623 424/489 |
| 2006/0193846 | A1 * | 8/2006 | Stimmeder | A61K 9/1647 424/94.64 |

* cited by examiner

*Primary Examiner* — Scott Long
*Assistant Examiner* — Sarah Alawadi
(74) *Attorney, Agent, or Firm* — Vivicar Law, PLLC

(57) ABSTRACT

Disclosed are solid and frozen haemostatic materials and dressings consisting essentially of a fibrinogen component and a fibrinogen activator. Also disclosed are methods of treating internal wounded tissue in a mammal by applying one or more of these haemostatic materials and dressings.

18 Claims, 1 Drawing Sheet

Ex Vivo Porcine Carotid Arteriotomy Assay Setup
EVCPA

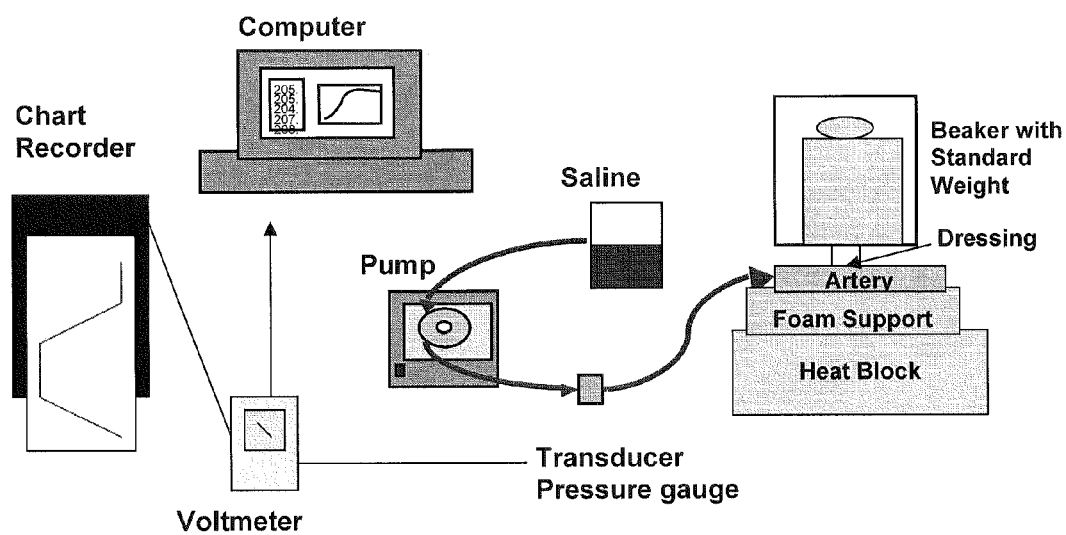

METHODS AND DRESSINGS FOR SEALING INTERNAL INJURIES

This application is a continuation of U.S. patent application Ser. No. 13/080,086, filed on Apr. 5, 2011, which is a continuation of U.S. patent application Ser. No. 12/222,277, filed on Aug. 6, 2008, which is a continuation-in-part application, and therefore claims benefit of the filing date, of prior U.S. Provisional Patent Application No. 60/935,311, all of which are herein incorporated by reference in their entirety.

FIELD OF THE INVENTION

The present invention relates to dressings for treating internal injured tissue in a mammalian patient, such as a human and methods of using the same.

BACKGROUND OF THE INVENTION

There are a large number of medical procedures that result in injuries to blood vessels. Similarly, there are numerous examples of bleeding caused by traumatic injuries, hematological disorders, and from unknown causes. When the site of bleeding is not readily accessible, such as an injured vessel located deep within the flesh, or inside a body cavity, a simple and effective method of hemorrhage control that can access the site within the body and seal the injured vessel is needed. Similarly, tissue may be divided by either traumatic injury or surgical procedure, and require sealing to approximate the edges of the injury in order to restore function. Current sealing products and devices have one or more deficiencies, usually due to their inadequate performance, or their reliance upon non-natural components that interfere with normal healing.

The need for improved technologies to address these injuries is significant. For example, in the case of blood vessels that have been deliberately punctured as part of a diagnostic and/or therapeutic procedure (such as cardiac catheterization, balloon angioplasty, vascular stenting and the like), over seven million such procedures are currently performed every year, but with a 9% overall complication rate and a 1-3% major completion rate (See Millennium Research Group: Global Markets for Vascular Closure Devices 2006). These complications can lead to significant morbidity, increased expense, a requirement for additional procedures and/or devices, extended time in the medical facility and conversion of outpatients to inpatients. Commercially available products now available only reduce the major complication rate by one half of one percent (See Arora et al: Am Heart J. 2007 April; 155(4):606-11) to 2.4%. Nevertheless, despite this poor performance, even these devices are currently used since the costs and consequences of procedure-induced complications is so high (See Resnic et al: Am J Cardiol. 2007 March 15; 99(6):766-70).

Not only are there the above described complications associated with therapy itself, closure of the access hole(s) created in the blood vessel is a significant source of additional complications, including uncontrolled hemorrhage, pseudoaneurysm, hematoma, arteriovenous fistula, arterial thrombosis, infection, and retained devices (See Meyers et al: *Angiographic Access Site Complications in the Era of Arterial Closure Devices* Vasc Endovasc Surg, 2002; 36 (2) 137-44). These additional complications may lead to prolonged closure procedures, hospitalization, the requirement for surgical repair, and even tissue loss or death.

Currently, the primary means of closing the access hole in the vessel has been to allow a natural blood clot to form at the puncture site. This has generally been accomplished by manual compression, but various products have recently been developed in an attempt to reduce the time required to achieve vascular closure. Such devices automate the application of pressure over the injury site, suture the hole in the vessel, clip the hole shut, or apply some sort of patch or pad that allegedly increases the formation of a natural clot at the site. These devices are convenient and gaining in popularity, but their overall safety appears over estimated. Indeed, far from being risk free, these devices may be associated with unique levels of hemorrhagic and cardiac risks including myocardial infarction, stroke and death (See Rao, S. *Implications of bleeding and blood transfusion in percutaneous coronary intervention*. Rev Cardiovasc Med. 2007, 8 Suppl 3:S18-26.).

Significant risks have been reported to be associated with all classes of vascular closure devices. Most seriously, the severity and the difficulty in treating complications are generally greater when vascular closure devices are used (See Nehler et al. *Iatrogenic vascular injuries from percutaneous vascular suturing devices*. J. Vasc Surg 2001 May; 33(5):943-7; Castelli et al: *Incidence of vascular injuries after use of the Angio-Seal closure device following endovascular procedures in a single center*. World J Surg. 2006 March, 30(3):280-4.). The use of such devices is even associated with higher risks among patients having complications of pseudoaneurysms, failure to successfully treat such pseudoaneurysms, blood loss, transfusions, extensive operations to correct the problems and arterial infections (See Sprouse et al. *The management of peripheral vascular complications associated with the use of percutaneous suture-mediated closure device*. J Vasc Surg. 2001 April; 33(4):688-693.). Moreover, some of these complications can be deadly, particularly in patients with diabetes, obesity and previously implanted devices (all conditions commonly found in patients in whom such closure devices are frequently used) (See Hollis and Rehring. *Femoral endarteritis associated with percutaneous suture closure new technology, challenging complications*. J Vasc Surg. 2003 July; 38(1):83-7.). Accordingly, there remains a great need to develop a vascular closure system that avoids the problems associated with use of known vascular closure devices.

Another medical situation involving treatment of injured internal tissue is the repair of herniations. There are numerous types and locations of hernia, and the surgical repair techniques vary widely depending thereon. Both open and endoscopic procedures are currently in use, and may involve the use of sutures alone or sutures in combination with various kinds of meshes or supports for the injured tissue. Major complications for most hernia repair procedures include pain and the requirement to re-do the repair (See American College of Surgeons. *When you need an operation . . . About Hernia Repair*, available at: http://www.facs.org/public_info/operation/hernrep.pdf).

Similarly, there is also a need to improve the therapeutic options for treatment of simple bleeding conditions such as epistaxis, which requires professional medical treatment in 1 of 7 people in their lifetime (See Evans: *Epistaxis*, emedicine (2007) available at www.emedicine.com/EMERG/topic806.htm). In fact, epistaxis is frequently cited as the most common ENT emergency (See Hussain et al: *Evaluation of aerology and efficacy of management protocols of epistaxis*. Ayub Med Coll Abottabad, 2006 October-December; 18(4);63-6) The difficulty in treating these cases is evidenced by the fact that 1.6 out of every 10,000 patients are hospitalized for epistaxis that is refractory to normal treatment (See Viehweg et al; *Epistaxis: diagnosis and treatment*, J. Oral Maxilofac Surg 2006 March; 64(3):5 11-8). Current treatment options include packing, chemical cauterization, electrocautery, surgical ligation and embolization (See: Ortiz & Bhattacharyya: *Management pitfalls in the use of embolization for the treatment of severe epistaxis*. Ear Nose Throat J. 2002 March; 82(3):178-83.) Frequently, multiple treatments with different technologies are required to effectively treat this often life-threatening condition (See Siniluoto et al: *Embolization for the treatment of posterior epistaxis. An analysis of 31 cases*. Arch Otolaryngol Head Neck Surg. 1993 August; 119(8):837-41; Gifford & Orlandi: *Epistaxis*. Otoloaryngol Clin North Am. 2008 June; 41(3):525-36, vii).

There are now in use a number of newer haemostatic agents that have been developed to overcome the deficiencies of traditional gauze bandages. These haemostatic agents include the following:

Microporous polysaccharide particles (TraumaDEX®, Medafor Inc., Minneapolis, Minn.);
Zeolite (QuikClot®, Z-Medica Corp, Wallington, Conn.);
Acetylated poly-N-acetyl glucosamine (Rapid Deployment Hemostat™ (RDH), Marine Polymer Technologies, Danvers, Mass.);
Chitosan (HemCon® bandage, HemCon Medical Technologies inc., Portland Oreg.);
Liquid Fibrin Sealants (Tisseel VH, Baxter, Deerfield, Ill.)
Human fibrinogen and thrombin on equine collagen (TachoComb-S, Hafslund Nycomed Pharma, Linz, Austria);
Microdispersed oxidized cellulose (m*doc™, Alltracel Group, Dublin, Ireland);
Propyl gallate (Hemostatin™, Analytical Control Systems Inc., Fishers, Ind.);
Epsilon aminocaproic acid and thrombin (Hemarrest™ patch, Clarion Pharmaceuticals, Inc);
Purified bovine corium collagen (Avitene® sheets (nonwoven web or Avitene Microfibrillar Collagen Hemostat (MCH), Davol, Inc., Cranston, R.I.);
Controlled oxidation of regenerated cellulose (Surgicel®, Ethicon Inc., Somerville, N.J.);
Aluminum sulfate with an ethyl cellulose coating (Sorbastace Microcaps, Hemostace, LLC, New Orleans, La.);
Microporous hydrogel-forming polyacrylamide (BioHemostat, Hemodyne, Inc., Richmond Va.); and
Recombinant activated factor VII (NovoSeven®, NovoNordisk Inc., Princeton, N.J.).

These agents have met with varying degrees of success when used in animal models of traumatic injuries and/or in the field, and with limited success in the sealing of therapeutic vascular injuries.

Liquid fibrin sealants, such as Tisseel VH, have been used for years as an operating room adjunct for hemorrhage control. See J. L. Garza et al., J. Trauma 30:512-513 (1990); H. B. Kram et al., J. Trauma 30:97-101(1990); M. G. Ochsner et al., J. Trauma 30:884-887 (1990); T. L. Matthew et al., Ann. Thorac. Surg. 50:40-44 (1990); H. Jakob et al., J. Vasc. Surg., 1:171-180 (1984). The first mention of tissue glue used for hemostasis dates back to 1909. See Current Trends in Surgical Tissue Adhesives: Proceedings of the First International Symposium on Surgical Adhesives, M. J. MacPhee et al., eds. (Lancaster, Pa.: Technomic Publishing Co; 1995). Liquid fibrin sealants are typically composed of fibrinogen and thrombin, but may also contain Factor XIII/XIIIa, either as a by-product of fibrinogen purification or as an added ingredient (in certain applications, it is therefore not necessary that Factor XIII/Factor XIIIa be present in the fibrin sealant because there is sufficient Factor XIII/XIIIa, or other transaminase, endogenously present to induce fibrin formation).

As liquids, however, these fibrin sealants have not proved useful outside certain specific procedures.

Dry fibrinogen-thrombin dressings having a collagen support (e.g. TachoComb™, TachoComb™ H and TachoSil available from Hafslund Nycomed Pharma, Linz, Austria) are also available for operating room use in many European countries. See U. Schiele et al., Clin. Materials 9:169-177 (1992). While these fibrinogen thrombin dressings do not require the pre-mixing needed by liquid fibrin sealants, their utility for field applications is limited by a requirement for storage at 4° C. and the necessity for pre-wetting with saline solution prior to application to the wound. These dressings are also not effective against high pressure, high volume bleeding. See Sondeen et al., J. Trauma 54:280-285 (2003).

A dry fibrinogen/thrombin dressing for treating wounded tissue is also disclosed in U.S. Pat. No. 6,762,336. This particular dressing is composed of a backing material and a plurality of layers, the outer two of which contain fibrinogen (but no thrombin) while the inner layer contains thrombin and calcium chloride (but no fibrinogen). While this dressing has shown great success in several animal models of hemorrhage, the bandage is fragile, inflexible, and has a tendency to break apart when handled. See McManus et al., Business Briefing: Emergency Medical Review 2005, at 78.; Kheirabadi et al., J. Trauma 59:25-35 (2005). In addition, U.S. Pat. No. 6,762,336 teaches that this bandage should contain 15 mg/cm$^2$ of fibrinogen to successfully pass a porcine arteriotomy test that is less robust than that disclosed in this application (see Example XI). Moreover, although U.S. Pat. No. 6,762,336 discloses that bandages comprising two layers of fibrinogen, each with a concentration of 4 mg/cm$^2$ to 15 mg/cm$^2$ may provide effective control of hemorrhage, it further teaches that "fibrinogen dose is related to quality. The higher dose is associated with more firm and tightly adhered clots. While lower fibrinogen doses are effective for hemorrhage control during the initial 60 minutes, longer term survival will likely depend on clot quality."

Other fibrinogen/thrombin-based dressings have also been proposed. For example, U.S. Pat. No. 4,683,142 discloses a resorptive sheet material for closing and healing wounds which consists of a glycoprotein matrix, such as collagen, containing coagulation proteins, such as fibrinogen and thrombin. U.S. Pat. No. 5,702,715 discloses a reinforced biological sealant composed of separate layers of fibrinogen and thrombin, at least one of which also contains a reinforcement filler such as PEG, PVP, BSA, mannitol, FICOLL, dextran, myo-inositol or sodium chlorate. U.S. Pat. No. 6,056,970 discloses dressings composed of a bioabsorbable polymer, such as hyaluronic acid or carboxymethylcellulose, and a haemostatic composition composed of powdered thrombin and/or powdered fibrinogen. U.S. Pat. No. 7,189,410 discloses a bandage composed of a backing material having thereon: (i) particles of fibrinogen; (ii) particles of thrombin; and (iii) calcium chloride. U.S. Patent Application Publication No. US 2006/0155234 A1 discloses a dressing composed of a backing material and a plurality of fibrinogen layers which have discrete areas of thrombin between them. To date, none of these dressings have been approved for use or are available commercially.

A number of different techniques, including the use of liquid fibrin sealant, have been proposed for sealing the punctures in blood vessels made to secure vascular access. For example, U.S. Pat. No. 7,357,794 discloses devices, systems and methods for acute or chronic delivery of substances or apparatus to extravascular treatment sites. U.S. Pat. No. 7,335,220 discloses apparatus and methods for sealing a vascular puncture using an expanding lyophilized hydrogel plug. U.S. Pat. No. 7,300,663 discloses adhesion and sealing of tissue with compositions containing polyfunctional crosslinking agents and protein polymers. U.S. Pat. No. 7,399,483 discloses a carrier with solid fibrinogen and solid thrombin; U.S. Pat. No. 7,335,220 discloses apparatus and methods for sealing vascular punctures. U.S. Pat. No. 7,115,588 discloses methods for treating a breach or puncture in a blood vessel. U.S. Pat. No. 7,008,442 discloses vascular sealant delivery devices using liquid formulations. U.S. Pat. No. 6,890,342 discloses to methods and apparatus for closing vascular puncture using a guidewire and/or other surgical implement extending from the wound on which a haemostatic material is moved into contact with an area of the blood vessel surrounding the wound. U.S. Pat. No. 6,818,008 discloses percutaneous puncture sealing method using flowable sealants. U.S. Pat. No. 6,699,262 discloses a percutaneous tissue track closure assembly and method using flowable materials. U.S. Pat. No. 6,613,070 discloses sealing vascular penetrations with haemostatic gels. U.S. Pat. No. 6,500,152 discloses a device for introducing a two-component liquid fibrin adhesive into a puncture channel. U.S. Pat. No. 6,325,789 also discloses a device for sealing puncture wounds using liquid or paste fibrin sealant. U.S. Pat. No. 5,814,066 discloses methods of reducing femoral arterial bleeding using percutaneous application of liquid fibrin sealant. U.S. Pat. No. 5,725,551, U.S. Pat. No. 5,486,195 and U.S. Pat. No. 5,443,481 each disclose the use of two component liquid fibrin sealant for artery closure. U.S. Pat. No. 5,649,959 discloses an assembly for sealing a puncture in a vessel which maintains the fibrinogen and thrombin separately. To date, however, all of these remain little-used in therapy, most likely due to the difficult and time consuming preparation requirements for two-component liquid fibrin sealant compositions.

Similarly, two component liquid fibrin sealants have been used to attach surgical meshes in the treatment of abdominal hernias. The surgical results have been excellent, typically as good or better than the efficacy of suture and staple fixation, with reduced complications and post-operative pain. (See Schwab et al., Hernia. 2006 June;10(3):272-7)

Liquid fibrin sealant has also be used to treat epistaxis, endoscopic sinus surgery and endonasal surgery ((See Vaiman et al. *Fibrin glue treatment for epistaxis*. Rhinology. 2002 June; 40(2):99-91; Vaiman et al. *Use of fibrin glue as a haemostatic in endoscopic sinus surgery*. Ann Otol Rhinol Laryngol, 2005 March; 114(3): 237-41; Vaiman et al. *Fibrin sealant: alternative to nasal packing in endonasal operations. A prospective randomized study*. Isr Med Assoc J. 2005 September; 7(9);571-4.). All these reports indicate that liquid fibrin sealant may be used with some success at controlling hemorrhage from various locations just inside the nose all the way into the sinuses. However, the time and efforts associated with preparing such sealants make them less than ideal for daily clinical use Accordingly, there remains a need in the art for solid dressings that can be used to achieve hemostasis and sealing of internal wounded tissue, particularly highly vascularized tissue, and single blood vessels. Additionally, treatment of tissues that have been divided (e.g. due to accident, pathology or surgical intervention) and require re-approximation to promote healing would also benefit from a solid dressing capable of adequate tissue sealing.

The assessment of such dressings requires new techniques that go beyond those previously disclosed for testing haemostatic dressings. The ability of dressings to seal an injured blood vessel has been determined by an ex vivo porcine arteriotomy (EVPA) performance test, which was first described in U.S. Pat. No. 6,762,336. The EVPA performance test evaluates the ability of a dressing to stop fluid flow through a hole in a porcine artery. While the procedure described in U.S. Pat. No. 6,762,336 has been shown to be useful for evaluating haemostatic dressings, it failed to replicate faithfully the requirements for success in vivo. More specifically, the procedure disclosed in U.S. Pat. No. 6,762,336 required testing at 37° C., whereas, in the real world, wounds are typically cooler than that. This decreased temperature can significantly reduce the rate of fibrin formation and its haemostatic efficacy in trauma victims. See, e.g., Acheson et al., J. Trauma 59:865-874 (2005). The test in U.S. Pat. No. 6,762,336 also failed to require a high degree of adherence of the dressing to the injured tissue. A failure mode in which fibrin forms but the dressing fails to attach tightly to the tissue would, therefore, not be detected by this test. Additionally, the pressure utilized in the procedure (200 mHg) may be exceeded during therapy for some trauma patients. The overall result of this is that numerous animal tests, typically involving small animals (such as rats and rabbits), must be conducted to accurately predict dressing performance in large animal, realistic trauma studies and in the clinical environment.

In order to minimize the amount of time and the number of animal studies required to develop dressings intended to treat accessible traumatic injuries, an improved ex vivo testing procedure has been developed. To accomplish this, the basic conditions under which the dressing test was conducted were changed, and the severity of the test parameters was increased to include testing at lower temperatures (i.e. 29-33° C. vs. 37° C., representing the real physiologic challenge at realistic wound temperatures (Acheson et al., J. Trauma 59:865-874 (2005)), higher pressures (i.e. 250 mmHg vs. 200 mmHg), a longer test period (3 minutes vs. 2 minutes) and larger sized arterial injuries (U.S. Pat. No. 6,762,336 used an 18 gauge needle puncture, whereas the revised procedure used puncture holes ranging from 2.8 mm to 4 mm×6 mm). A new test has also been developed to directly measure adherence of the dressing to the injured tissue. Both these tests showed greatly improved stringency and are thus capable of surpassing the previous ex vivo test and replacing many in vivo tests for efficacy. These newer tests are described in U.S. patent application Ser. No. 11/882,874, the disclosure of which is herein incorporated by reference in its entirety.

The newer tests described in U.S. patent application Ser. No. 11/882,874 were designed to simulate trauma-derived, accessible wounds with high pressure and flow characteristics. Therefore, for the evaluation of methods and compositions for treating wounded internal tissue, it was preferable to develop additional assays to more accurately simulate the peripheral vasculature and the effects of grounding tissue.

SUMMARY OF THE INVENTION

It is therefore an object of the present invention to provide solid dressings that can treat wounded internal mammalian tissue. It is further an object of the present invention to provide a method of treating wounded internal mammalian tissue, particularly human tissue. Other objects, features and advantages of the present invention will be set forth in the detailed description of preferred embodiments that follows, and will in part be apparent from that description and/or may be learned by practice of the present invention. These objects and advantages will be realized and attained by the compositions and methods described in this specification and particularly pointed out in the claims that follow.

In accordance with these and other objects, a first embodiment of the present invention is directed to a method for treating wounded internal tissue in a mammal comprising applying to wounded internal tissue at least one haemostatic material consisting essentially of a fibrinogen component and a fibrinogen activator for a time sufficient to reduce the flow of fluid from the wounded tissue, wherein the haemostatic material is substantially homogeneous.

Another embodiment is directed to a method for treating wounded internal tissue in a mammal comprising applying to wounded internal tissue at least one haemostatic material consisting essentially of a fibrinogen component and a fibrinogen activator for a time sufficient to reduce the flow of fluid from the wounded tissue, wherein the haemostatic material is cast or formed from a single aqueous solution containing he fibrinogen component and the fibrinogen activator.

Another embodiment is directed to a method for treating wounded internal tissue in a mammal composing applying to wounded internal tissue at least one haemostatic material consisting essentially of a fibrinogen component and a fibrinogen activator for a time sufficient to reduce the flow of fluid from the wounded tissue, wherein the haemostatic material is cast or formed as a single piece.

Still other embodiments of the invention are directed to the various solid and frozen haemostatic materials useful in the inventive methods.

It is to be understood that the foregoing general description and the following detailed description of preferred embodiments are exemplary and explanatory only and are intended to provide further explanation, but not limitation, of the invention as claimed herein.

BRIEF DESCRIPTION OF DRAWINGS

FIG. 1 is a diagram of the set-up for the ex vivo porcine carotid arteriotomoy assay described herein.

DETAILED DESCRIPTION OF PREFERRED EMBODIMENTS

Unless defined otherwise, all technical and scientific terms used herein have the same meaning as is commonly understood by one of skill in the art to which this invention belongs. All patents and publications mentioned herein are incorporated by reference.

As used herein, use of a singular article such as "a," "an," and "the" is not intended to excluded pluralities of the article's object unless the context clearly and unambiguously dictates otherwise.

"Patient" as used herein refers to human or animal individuals in need of medical care and/or treatment.

"Wound" or "wounded tissue" as used herein refers to any damage to any internal tissue of a patient which results in the loss of blood from the circulatory system and/or any other fluid from the patient's body. The tissue may be any mammalian internal tissue, such as an organ or blood vessel. A wound may be in a soft internal tissue, such as an organ, or in hard internal tissue, such as bone. The "damage" may have been caused by any agent or source, including traumatic injury, infection or surgical intervention. Thus, the "damage" being treated according to the methods of the present invention may be the result of either an accident or an intentional act.

"Resorbable material" as used herein refers to a substance that is broken down spontaneously and/or by the mammalian body into components which are consumed or eliminated in such a manner as not to interfere significantly with wound healing and/or tissue regeneration, and without causing any significant metabolic disturbance.

"Stability" as used herein refers to the retention of those characteristics of a substance that determine activity and/or function.

"Suitable" as used herein is intended to mean that a substance (or mixture of substances) does not adversely affect the stability of the dressings or any component thereof.

"Binding agent" as used herein refers to a compound or mixture of compounds that improves the adherence and/or cohesion of the components of the haemostatic material of the dressings.

"Solubilizing agent" as used herein refers to a compound or mixture of compounds that improves the dissolution of a protein or proteins in aqueous solvent.

"Filler" as used herein refers to a compound or mixture of compounds that provide bulk and/or porosity to the haemostatic material.

"Release agent" as used herein refers to a compound or mixture of compounds that facilitates removal of a dressing from a manufacturing mold.

"Foaming agent" as used herein refers to a compound or mixture of compounds that produces gas when hydrated under suitable conditions.

"Solid" as used herein is intended to mean that a haemostatic material or dressing will not substantially change in shape or form when placed on a rigid surface and then left to stand at room temperature for 24 hours.

"Frozen" as used herein is intended to mean that a haemostatic material or dressing will not substantially change in shape or form when placed on a rigid surface and then left to stand at 0° C. for 24 hours, but substantially change in shape or form when placed on a rigid surface and then left at room temperature for 24 hours. Thus, in the context of the present invention, a "solid" dressing is not "frozen" and a "frozen" composition is not "solid".

"Substantially homogeneous" as used herein is intended to mean that the haemostatic material has a uniform composition throughout, within the tolerances described herein. Thus, a "substantially homogeneous" haemostatic material according to the present invention may be composed of a plurality of particles, provided that each of those particles has the same composition.

A first preferred embodiment of the present invention is directed to a method for treating wounded internal tissue in a mammal comprising applying to wounded internal tissue at least one haemostatic material consisting essentially of a fibrinogen component and a fibrinogen activator for a time sufficient to reduce the flow of fluid from the wounded tissue, wherein the haemostatic material is substantially homogeneous.

Another embodiment is directed to a method for treating wounded internal tissue in a mammal comprising applying to wounded internal tissue at least one haemostatic material consisting essentially of a fibrinogen component and a fibrinogen activator for a time sufficient to reduce the flow of fluid from the wounded tissue, wherein the haemostatic material is cast or formed from a single aqueous solution containing the fibrinogen component and the fibrinogen activator.

Another embodiment is directed to a method for treating wounded internal tissue in a mammal comprising applying to wounded internal tissue at least one haemostatic material consisting essentially of a fibrinogen component and a fibrinogen activator for a time sufficient to reduce the flow of fluid from the wounded tissue, wherein the haemostatic material is cast or formed as a single piece.

Another preferred embodiment is directed to a frozen haemostatic material for treating wounded internal tissue in a mammal consisting essentially of a fibrinogen component and a fibrinogen activator.

As used herein, "consisting essentially of" is intended to mean that the fibrinogen component and the fibrinogen activator are the only necessary and essential ingredients of the haemostatic material when it is used as intended to treat wounded internal tissue. Accordingly, the haemostatic material may contain other ingredients in addition to the fibrinogen component and the fibrinogen activator as desired for a particular application, but these other ingredients are not required for the solid dressing to function as intended under normal conditions, i.e. these other ingredients are not necessary for the fibrinogen component and fibrinogen activator to react and form enough fibrin to reduce the flow of blood and/or fluid from normal wounded tissue when that dressing is applied to that tissue under the intended conditions of use. If, however, the conditions of use in a particular situation are not normal, for example the patient is a hemophiliac suffering from Factor XIII deficiency, then the appropriate additional components, such as Factor XIII/XIIIa or some other transaminase, may be added to the haemostatic material without deviating from the spirit of the present invention.

According to certain embodiments of the present invention, the haemostatic material is formed or cast as a single piece. Once such is formed or cast, the haemostatic material may then be used as is or it may be further processed, for example by grinding into a powder of pre-determined particle size. Such particles may then be used as is or may be combined with other substances for a particular application, e.g. such particles of haemostatic material may be mixed with a foaming agent or aerosol gas or may be combined with one or more binding agents and applied to a support material.

The haemostatic materials of the present invention may be formed or cast in any shape or form suitable for a given application. For example, the haemostatic material may be formed or cast in the shape of a cone or cylinder or the like. Such a shape is particularly suitable for use in applications where the damage to the tissue being treated is a hole to be plugged or sealed, e.g. a vein which has been intentionally punctured as part of a medical procedure, such as angioplasty. In such applications, the haemostatic material may alternatively be in the shape of a disk, optionally with a hole for use in conjunction with a guide wire. Additionally, each of these forms can also be prepared by combining particles of the inventive haemostatic materials with at least one suitable binding agent in an appropriate mold.

The haemostatic material may also be formed or cast in the shape of a flat sheet. Such a form is particularly suitable for use in implications where tissue needs to be sealed or approximated, for example in connection with endoscopic surgery or, hernia repair. Alternatively, a flat sheet may be prepared by combining particles of the inventive haemostatic materials with one or more suitable binding agents, optionally in a mold.

The haemostatic material may also optionally contain one or more suitable fillers, such as sucrose, lactose, maltose, silk, fibrin, collagen, albumin (natural or recombinantly produced), polysorbate (Tween™), chitin, chitosan and its derivatives (e.g. NOCC-chitosan), alginic acid and salts thereof, cellulose and derivatives thereof, proteoglycans, hyaluron and its derivatives, such as hyaluronic acid, glycolic acid polymers, lactic acid polymers, glycolic acid/lactic acid co-polymers, and mixtures of two or more thereof.

The haemostatic material may also optionally contain one or more suitable solubilizing agents, including detergents and tensides. Illustrative examples of suitable solubilizing agents include, but are not limited to, the following: sucrose, dextrose, mannose, trehalose, mannitol, sorbitol, albumin, hyaluron and its derivatives, such as hyaluronic acid, sorbate, polysorbate (Tween™), sorbitan (SPAN™) and mixtures of two or more thereof.

The haemostatic material may also optionally contain one or more suitable foaming agents, such as a mixture of a physiologically acceptable acid (e.g. citric acid or acetic acid) and a physiologically suitable base (e.g. sodium bicarbonate or calcium carbonate). Other suitable foaming agents include, but are nor limited to, dry particles containing pressurized gas, such as sugar particles containing carbon dioxide (see, e.g., U.S. Pat. No. 3,012,893) or other physiologically acceptable gases (e.g. Nitrogen or Argon), and pharmacologically acceptable peroxides. Such a foaming agent may be introduced into the aqueous mixture of the fibrinogen component and the fibrinogen activator, or may be introduced into an aqueous solution of the fibrinogen component and/or an aqueous solution of the fibrinogen activator prior to mixing. Alternatively, the inventive haemostatic materials may be ground to particles of a predetermined size and then combined with a suitable foaming agent.

The haemostatic material may also optionally contain a suitable source of calcium ions, such as calcium chloride, and/or a fibrin cross-linker, such as a transaminase (e.g. Factor XIII/XIIIa) or glutaraldehyde.

The haemostatic materials of the present invention are most preferably prepared by mixing aqueous solutions of the fibrinogen component and the fibrinogen activator under conditions which minimize the activation of the fibrinogen component by the fibrinogen activator. This aqueous mixture of the fibrinogen component and the fibrinogen activator may then be frozen until used to treat wounded tissue. Alternatively, the mixture may then subjected to a process, such as lyophilization or freeze-drying, to reduce the moisture content to a predetermined effective level, i.e. to a level where the dressing is solid and therefore will not substantially change in shape or form upon standing at room temperature for 24 hours. Similar processes that achieve the same result, such as drying, spray-drying, vacuum drying and vitrification, may also be employed, either alone or in combination.

As used herein, "moisture content" refers to levels determined by procedures substantially similar to the FDA-approved, modified Karl Fischer method (Centers for Biologics Evaluation and Research, FDA, Docket No. 89D-0140, 83-93; 1990 and references cited therein) or by near infrared spectroscopy. Suitable moisture content(s) for a particular inventive haemostatic material may be determined empirically by one skilled in the art depending upon the intended application(s) thereof.

For example, in certain embodiments of the present invention, higher moisture contents are associated with more flexible solid dressings. Thus, in solid dressings intended to be deformed in use, it may be preferred for the haemostatic material to have a moisture content of at least 6% and even more preferably in the range of 6% to 44%.

Similarly, in other embodiments of the present invention, lower moisture contents are associated with more rigid solid dressings. Thus, in solid dressings intended to be used as formed or cast, it may be preferred for the haemostatic material to have a moisture content of less than 6% and even more preferably in the range of 1% to 6%.

Accordingly, illustrative examples of suitable moisture contents for the inventive haemostatic materials include, but are not limited to, the following (each value being ±0.9%): less than 53%; less than 44%; less than 28%; less than 24%;

less than 16%; less than 12%; less than 6%; less than 5%; less than 4%; less than 3%; less than 2.5%; less than 2%; less than 1.4%; between 0 and 12%, non inclusive; between 0 and 6%; between 0 and 4%; between 0 and 3%; between 0 and 2%; between 0 and 1%; between 1 and 16%; between 1 and 11%; between 1 and 8%; between 1 and 6%; between 1 and 4%; between 1 and 3%; between 1 and 2%; and between 2 and 4%.

The fibrinogen component in the haemostatic material may be any suitable fibrinogen known and available to those skilled in the art. The fibrinogen component may also be a functional derivative or metabolite of a fibrinogen, such the fibrinogen α, β and/or γ chains, soluble fibrin I or fibrin II, or a mixture of two or more thereof. A specific fibrinogen (or functional derivative or metabolite) for a particular application may be selected empirically by one skilled in the art. As used herein, the term "fibrinogen" is intended to include mixtures of fibrinogen and small mounts of Factor XIII/Factor XIIIa, or some other such transaminase. Such small amounts are generally recognized by those skilled in the art as usually being found in mammalian fibrinogen after it has been purified according to the methods and techniques presently known and available in the art, and typically range from 0.1 to 20 Units/mL.

Preferably, the fibrinogen employed as the fibrinogen component is a purified fibrinogen suitable for introduction into a mammal. Typically, such fibrinogen is a part of a mixture of human plasma proteins which include Factor XIII/XIIIa and have been purified to an appropriate level and virally inactivated. A preferred aqueous solution of fibrinogen for preparation of a solid dressing contains around 37.5 mg/mL fibrinogen at a pH of around 7.4±0.1. Suitable fibrinogen for use as the fibrinogen component has been described in the art, e.g. U.S. Pat. No. 5,716,645, and similar materials are commercially available, e.g. from sources such as Sigma-Aldrich, Enzyme Research Laboratories, Haematologic Technologies and Aniara.

The fibrinogen component should be present in the inventive haemostatic materials in an amount effective to react with the fibrinogen activator and form sufficient fibrin to reduce the flow of fluid from wounded internal tissue. According to certain preferred embodiments of the present invention, when the haemostatic material is frozen, the fibrinogen component is present in an amount of from 4.70 mg to 18.75 mg (±0.009 mg) per square centimeter of the surface(s) of the haemostatic material intended to contact the wounded internal tissue.

According to other preferred embodiments, when the haemostatic material is a solid, regardless of form, the fibrinogen component is present in an amount of from 5.00 mg to 450.00 mg (±0.009 mg) per square centimeter of the surface(s) intended to contact the wounded internal tissue being treated. Greater or lesser amounts, however, may be employed depending upon the particular application intended for the solid dressing.

For example, when the haemostatic material is in the shape of a rod or cylinder, the fibrinogen component is more preferably present in an amount of from 25.00 mg to 75.00 mg (±0.009 mg) per square centimeter of the surface(s) intended to contact the wounded internal tissue being treated. Alternatively, when the haemostatic material is in the shape of a flat sheet or disk, the fibrinogen component is more preferably present in an amount of from 5.00 to 56.00 mg (±0.009 mg) per square centimeter of the surface(s) intended to contact the wounded internal tissue being treated. Still alternatively, when the haemostatic material is powdered, either loose or compressed, the fibrinogen component is more preferably present in an amount from 26.00 mg to 450.00 mg (±0.09 mg) per square centimeter of the surface(s) intended to contact the wounded internal tissue being treated.

The fibrinogen activator employed in the haemostatic materials of the present invention may be any of the substances or mixtures of substances known by those skilled in the art to convert fibrinogen (or a fibrinogen equivalent) into fibrin. Illustrative examples of suitable fibrinogen activators include, but are not limited to, the following: thrombins, such as human thrombin or bovine thrombin, and prothrombins, such as human prothrombin or prothrombin complex concentrate (a mixture of Factors II, VII, IX and X); snake venoms, such as batroxobin, reptilase (a mixture of batroxobin and Factor XIIIa), bothrombin, calobin, fibrozyme, and enzymes isolated from the venom of Bothrops jararacussu; and mixtures of any two or more of these. See, e.g., Dascombwe et al., Thromb. Haemost. 78:947-51 (1997); Hahn et al., J. Biochem. (Tokyo) 119:835-43 (1996); Fortova et al., J. Chromatogr. S. Biomed. Appl. 694:49-53 (1997); and Andriao-Escarso et al., Toxicon. 35:1043-52 (1997).

Preferably, the fibrinogen activator is a thrombin. More preferably, the fibrinogen activator is a mammalian thrombin, although bird and/or fish thrombin may also be employed in appropriate circumstances. While any suitable mammalian thrombin may be used, the thrombin employed is preferably a lyophilized mixture of human plasma proteins which has been sufficiently purified and virally inactivated for the intended use of the solid dressing. Suitable thrombin is available commercially from sources such as Sigma-Aldrich, Enzyme Research Laboratories, Haematologic Technologies and Biomol International. A particularly preferred aqueous solution of thrombin for preparing the inventive haemostatic materials contains thrombin at a potency of between 10 and 2000±50 International Units/mL, and more preferred at a potency of 25±2.5 International Units/mL. Other constituents may include albumin (generally about 0.1 mg/mL) and glycine (generally about 100 mM±0.1 mM). The pH of this particularly preferred aqueous solution of thrombin is generally in the range of 6.5-7.8, and preferably 7.4±0.1, although a pH in the range of 5.5-8.5 may be acceptable.

In addition to the inventive haemostatic material(s), the solid and frozen dressings of the present invention may optionally further comprise one or more support materials. As used herein, a "support material" refers to a material that sustains or improves the structural integrity of the solid or frozen dressing and/or the fibrin clot formed when such a dressing is applied to wounded tissue. The support material may be an internal support material or a surface support material. Moreover, in the case of the latter, if the dressing is in a form that has a wound facing side, the support material may be on the wound facing side or it may be on the non-wound facing side or both.

Any suitable resorbable material known and available to those skilled in the art may be employed in the present invention. For example, the resorbable material may be a proteinaceous substance, such as silk, fibrin, keratin, collagen and/or gelatin. Alternatively, the resorbable material may be a carbohydrate substance, such as alginates, chitin, cellulose, proteoglycans (e.g. poly-N-acetyl glucosamine), glycolic acid polymers, lactic acid polymers, or glycolic acid/lactic acid co-polymers. The resorbable material may also comprise a mixture of proteinaceous substances or a mixture of carbohydrate substances or a mixture of both proteinaceous substances and carbohydrate substances. Specific resorbable material(s) may be selected empirically by those skilled in the art depending upon the intended use of the solid dressing.

According to certain preferred embodiments of the present invention, the resorbable material is a carbohydrate substance. Illustrative examples of particularly preferred resorbable materials include, but are not limited to, the materials sold under the trade names Vicryl™ (a glycolic acid/lactic acid copolymer) and Dexon™ (a glycolic acid polymer).

Any suitable non-resorbable material known and available to those skilled in the art may be employed as the support material. Illustrative examples of suitable non-resorbable materials include, but are not limited to, plastics, silicone polymers, paper and paper products, latex, gauze plastics, non-resorbable suture materials, latexes and suitable derivatives thereof.

According to other preferred embodiments, the support material comprises an internal support material. Such an internal support material is preferably fully contained within the haemostatic material(s) of a solid or frozen dressing. The internal support material may take any form suitable for the intended application of the haemostatic material. For example, according to certain embodiments, the internal support material may be particles of a predetermined suitable size which are dispersed throughout the haemostatic material. Alternatively, a sheet or film or internal support material may be included in the solid or frozen haemostatic material.

According to still other preferred embodiments, the support material may comprise a backing material on the surface(s) of the dressing opposite the wound-facing surface. As with the internal support material, the backing material may be a resorbable material or a non-resorbable material, or a mixture thereof, such as a mixture of two or more resorbable materials or a mixture of two or more non-resorbable materials or a mixture of resorbable material(s) and non-resorbable material(s).

According to still other preferred embodiments, the dressing comprises both a backing material and an internal support material in addition to the haemostatic material(s). According to still other preferred embodiments, the dressing comprises both a front support material and an internal support material in addition to the haemostatic layer(s). According to still other preferred embodiments, the dressing comprises a backing material, a front support material and an internal support material in addition to the haemostatic layer(s).

According to certain preferred embodiments, the haemostatic material(s) may also contain a binding agent to maintain the physical integrity of the haemostatic material(s). Illustrative examples of suitable binding agents include, bur are not limited to, sucrose, mannitol, sorbitol, gelatin, hyaluron and its derivatives, such as hyaluronic acid, maltose, povidone, starch, chitosan and its derivatives, and cellulose derivatives, such as carboxymethylcellulose, as well as mixtures of two or more thereof.

According to certain embodiments of the present invention, particularly where the solid or frozen dressing is manufactured using a mold, the dressings may also optionally further comprise a release layer in addition to the haemostatic material(s) and support layer(s). As used herein, a "release layer" refers to a layer containing one or more agents ("release agents") which promote or facilitate removal of the solid or frozen dressing from a mold in which it has been manufactured. A preferred such agent is sucrose, but other suitable release agents include gelatin, hyaluron and its derivatives, including hyaluronic acid, mannitol, sorbitol and glucose. Alternatively, such one or more release agents may be contained in the haemostatic material.

The haemostatic material and any layer(s) may be affixed to one another by any suitable means known and available to those skilled in the art. For example, a physiologically-acceptable adhesive may be applied to a backing material (when present), and the haemostatic material subsequently affixed thereto.

In certain embodiments of the present invention, the physiologically-acceptable adhesive has a shear strength and/or structure such that the backing material can be separated from the fibrin clot formed by the haemostatic layer after application of the dressing to wounded tissue. In other embodiments, the physiologically-acceptable adhesive has a shear strength and/or structure such that the backing material cannot be separated from the fibrin clot after application of the bandage to wounded tissue.

Suitable fibrinogen components and suitable fibrinogen activators for the haemostatic materials may be obtained from any appropriate source known and available to those skilled in the art, including, but not limited to, the following: from commercial vendors, such as Sigma-Aldrich and Enzyme Research Laboratories; by extraction and purification from human or mammalian plasma by any of the methods known and available to those skilled in the art; from supernatants or pastes derived from plasma or recombinant tissue culture, viruses, yeast, bacteria, or the like that contain a gene that expresses a human or mammalian plasma protein which has been introduced according to standard recombinant DNA techniques; and/or from the fluids (e.g. blood, milk, lymph, urine or the like) of transgenic mammals (e.g. goats, sheep, cows) that contain a gene which has been introduced according to standard transgenic techniques and that expresses the desired fibrinogen and/or desired fibrinogen activator.

According to certain preferred embodiments of the present invention, the fibrinogen component is a mammalian fibrinogen such as bovine fibrinogen, porcine fibrinogen, ovine fibrinogen, equine fibrinogen, caprine fibrinogen, feline fibrinogen, canine fibrinogen, murine fibrinogen or human fibrinogen. According to other embodiments, the fibrinogen component is bird fibrinogen or fish fibrinogen. According to any of these embodiments, the fibrinogen component may be recombinantly produced fibrinogen or transgenic fibrinogen.

According to certain preferred embodiments of the present invention, the fibrinogen activator is a mammalian thrombin, such as bovine thrombin, porcine thrombin, ovine thrombin, equine thrombin, caprine thrombin, feline thrombin, canine thrombin, murine thrombin and human thrombin. According to other embodiments, the thrombin is bird thrombin or fish thrombin. According to any of these embodiments, the thrombin may be recombinantly produced thrombin or transgenic thrombin.

As a general proposition, the purity of the fibrinogen component and/or the fibrinogen activator for use in the solid dressing will be a purity known to one of ordinary skill in the relevant art to lead to the optimal efficacy and stability of the protein(s). Preferably, the fibrinogen component and/or the fibrinogen activator has been subjected to multiple purification steps, such as precipitation, concentration, diafiltration and affinity chromatography (preferably immunoaffinity chromatography), to remove substances which cause fragmentation, activation and/or degradation of the fibrinogen component and/or the fibrinogen activator during manufacture, storage and/or use of the solid dressing. Illustrative examples of such substances that are preferably removed by purification include: protein contaminants, such as inter-alpha trypsin inhibitor and pre-alpha trypsin inhibitor; non-protein contaminants, such as lipids; and mixtures of protein and non-protein contaminants, such as lipoproteins. The fibrinogen component and/or fibrinogen activator and/or inventive haemostatic materials may also be subjected to suitable sterilization treatments, including, but not limited to, treatment with one or more of the following: heat, gamma radiation, e-beam radiation, plasma radiation and ethylene oxide.

The amount of the fibrinogen activator employed in the solid dressing is preferably selected to optimize both the efficacy and stability thereof. As such, a suitable concentration for a particular application of the solid dressing may be determined empirically by one skilled in the relevant art.

According to certain preferred embodiments of the present invention, when the fibrinogen activator is human thrombin, the amount of human thrombin employed is between 0.03 and 16.10 Units (all values being ±0.009) per square centimeter of the surface(s) of the haemostatic material intended to contact the wounded internal tissue. Greater or lesser amounts, however, may be employed depending upon the particular application intended for the solid dressing.

For example, when the haemostatic material is a solid in the shape of a rod or cylinder, the fibrinogen activator is more preferably present in an amount of from 2.50 Units to 7.50 Units (±0.009 Units) per square centimeter of the surface(s) intended to contact the wounded internal tissue being treated. Alternatively, when the haemostatic material is a solid in the shape of a flat sheet or disk, the fibrinogen activator is more preferably present in an amount of from 0.03 Units to 16.10 Units (±0.009 Units) per square centimeter of the surface(s) intended to contact the wounded internal tissue being treated. Still alternatively, when the haemostatic material is a powdered solid, either loose or compressed, the fibrinogen activator is more preferably present in an amount of about 1.3 Units (±0.00 mg) per square centimeter of the surface(s) intended to contact the wounded internal tissue being treated. Still alternatively, when the haemostatic material is frozen, the fibrinogen activator is more preferably present in an amount of about 1.3 Units (±0.09 mg) per square centimeter of the surface(s) intended to contact the wounded internal tissue being treated.

According to still other preferred embodiments of the present invention, when the fibrinogen activator is human thrombin, the amount of human thrombin employed is between 0.0087 and 1.0000 Units (all values being ±0.00009) per milligram of the fibrinogen component. Greater or lesser amounts, however, may be employed depending upon the particular application intended for the solid dressing.

For example, when the haemostatic material is a solid in the shape of a rod or cylinder, the fibrinogen activator is more preferably present in an amount of about 0.1 Units (±0.09 Units) per milligram of the fibrinogen component. Alternatively, when the haemostatic material is a solid in the shape of a flat sheet or disk, the fibrinogen activator is more preferably present in an amount of from 0.1 Units to 1.00 Units (±0.009 Units) per milligram of the fibrinogen component. Still alternatively, when the haemostatic material is a powdered solid, either loose or compressed, the fibrinogen activator is more preferably present in an amount of about 0.0087 Units to 0.0500 Units (±0.00009 Units) per milligram of the fibrinogen component. Still alternatively, when the haemostatic material is frozen, the fibrinogen activator is more preferably present in an amount of about 0.07 Units to 0.10 Units (±0.009 Units) per milligram of the fibrinogen component.

During use of the inventive haemostatic materials, the fibrinogen component and the fibrinogen activator are preferably activated at the time the dressing is applied to the wounded tissue by the endogenous fluids of the patient escaping from the hemorrhaging wound. Alternatively, in situations where fluid loss from the wounded tissue is insufficient to provide adequate hydration of the protein layers, the fibrinogen component and/or the fibrinogen activator may be activated by a suitable, physiologically-acceptable liquid, optionally containing any necessary co-factors and/or enzymes, prior to or during application of the dressing to the wounded tissue.

In some embodiments of the present invention, the inventive haemostatic materials may also contain one or more supplements, such as growth factors, drugs, polyclonal and monoclonal antibodies and other compounds. Illustrative examples of such supplements include, but are not limited to, the following: fibrinolysis inhibitors, such as aprotonin, tranexamic acid and epsilon-amino-caproic acid; antibiotics, such as tetracycline and ciprofloxacin, amoxicillin, and metronidazole; anticoagulants, such as activated protein C, heparin, prostacyclins, prostaglandins (particularly ($PGI_2$), leukotrienes, antithrombin III, ADPase, and plasminogen activator; steroids, such as dexamethaxone, inhibitors of prostacyclin, prostaglandins, leukotrienes and/or kinins to inhibit inflammation; cardiovascular drugs, such as calcium channel blockers, vasodilators and vasoconstrictors, such as epinephrine; chemoattractants; local anesthetics such as bupivacaine; and antiproliferative/antitumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as alpha- or beta- or gamma-Interferon, alpha- or beta-tumor necrosis factor, and interleukins; colony stimulating factors; erythropoietin; antifungals, such as diflucan, ketaconizole and nystatin; antiparasitic gents, such as pentamidine; antiinflammatory agents, such as alpha-1-anti-trypsin and alpha-1-antichymotrypsin; anesthetics, such as bupivacaine; analgesics; antiseptics, hormones; vitamins and other nutritional supplements; glycoproteins; fibronecton; peptides and proteins; carbohydrates (both simple and/or complex); proteoglycans; antiangiogenins; antigens; lipids or liposomes; oligonucleotides (sense and/or antisense DNA and/or RNA); and gene therapy reagents. In other embodiments of the present invention, the backing layer and/or the internal support layer, if present, may contain one or more supplements. According to certain preferred embodiments of the present invention, the therapeutic supplement is present in an amount greater than its solubility limit in fibrin.

The inventive haemostatic materials, and the solid and frozen dressings containing them, may be applied to any internal wounded tissue in a mammal using any of the suitable techniques and/or devices known and available to one skilled in the medical arts. For example, when used to treat vascular punctures, the haemostatic material(s) may be applied via a catheter, either with or without a guide wire. The inventive materials and dressings may also be applied in conjunction with endoscopic techniques, including endoscopic surgery, laparoscopic surgery and tele-robotic/tele-prescesne surgery. According to such embodiments, it is preferable to use a "plunger" or "tamper" to facilitate passage of the inventive materials through surrounding tissue to the wounded internal tissue being treated. The inventive materials and dressings may also be applied manually.

The following examples are illustrative only and are not intended to limit the scope of the invention as defined by the appended claims. It will be apparent to those skilled in the art that various modifications and variations can be made in the methods of the present invention ... without departing from the spirit and scope of the invention. Thus, it is intended that the present invention cover the modifications and variations of this invention provided they come within the scope of the appended claims and their equivalents.

EXAMPLES

The following is a list of acronyms used in the Examples below:

CFB: Complete Fibrinogen Buffer (100 mM Sodium Chloride, 1.1 mM Calcium Chloride, 10 mM Tris, 10 mM Sodium Citrate, 1.5% Sucrose, Human Serum Albumin (80 mg/g of total protein) and Tween™ 80 (non-animal source) 15 mg/g total protein)

CTB: Complete Thrombin Buffer (150 mM Sodium Chloride, 40 mM Calcium Chloride, 10 mM Tris and 100 mM L-Lysine with the addition of HSA at 100 ug/ml)

ERL: Enzyme Research Laboratories

EVPA: Ex Vivo Porcine Arteriotomy

EVPCA: Ex Vivo Porcine Carotid Arteriotomy

FD: Inventive haemostatic dressing

HSA: Human Serum Albumin

HD: A "sandwich" fibrin sealant haemostatic dressing as disclosed in U.S. Pat. No. 6,762,336

IFB: Incomplete Fibrinogen Buffer.; CFB without HSA and Tween

Fibrinogen Dose: In a solid mass, the amount of fibrinogen within the mass divided by the surface area to be treated. Usually expressed in mg of Fibrinogen per $cm^2$, where the mass of fibrinogen is determined via a clottable protein assay PETG: Glycol-modified Polyethylenetetrapthalate PPG: Polypropylene PVC: Poly vinyl chloride T:F Thrombin to Fibrinogen ratio. In a test article, the amount of thrombin activity per unit of fibrinogen. Usually expressed in thrombin NIH Units per mg of fibrinogen (measured via a clottable protein assay)

Thrombin Dose: In a solid mass, the amount of thrombin within the mass divided by the surface area to be treated. Usually expressed in NIH Units of thrombin per $cm^2$ TRIS: trishydroxymethylaminomethane (2-amino-2-hydroxymethyl-1,3-propanediol)

The ability of the dressings to seal an injured blood vessel was determined by modifications of an ex vivo porcine arteriotomy (EVPA) performance test, which was first described in U.S. Pat. No. 6,762,336. The EVPA performance test evaluates the ability of a dressing to stop fluid flow through a hole in a porcine artery. While the procedure described in U.S. Pat. No. 6,762,336 has been shown to be useful for evaluating haemostatic dressings, it failed to replicate faithfully the requirements for success in vivo. More specifically, the procedure disclosed in U.S. Pat. No. 6,762,336 requited testing at 37° C., whereas, in the real world, wounds are typically cooler than that. This decreased temperature can significantly reduce the rate of fibrin formation and its haemostatic efficacy in trauma victims. See, e.g., Acheson et al., J. Trauma 59:865-874 (2005). The test in U.S. Pat. No. 6,762,336 also failed to require a high degree of adherence of the dressing to the injured tissue. A failure mode in which fibrin forms but the dressing fails to attach tightly to the tissue would, therefore, not be detected by this test. Additionally, the pressure utilized in the procedure (200 mHg) may be exceeded during therapy for some trauma patients. The overall result of this is that numerous animal tests, typically involving small animals (such as rats and rabbits), must be conducted to accurately predict dressing performance in large animal, realistic trauma studies and in the clinical environment.

In order to minimize the amount of time and the number of animal studies required to develop the present invention, an improved ex vivo testing procedure was developed. To accomplish this, the basic conditions under which the dressing test was conducted were changed, and the severity of the test parameters was increased to include testing at lower temperatures (i.e. 29-33° C. vs. 37° C., representing the real physiologic challenge at realistic wound temperatures (Acheson et al., J. Trauma 59:865-874 (2005)), higher pressures (i.e. 250 mmHG vs. 200 mmHg), a longer test period (3 minutes vs. 2 minutes) and larger sized arterial injuries (U.S. Pat. No. 6,762,336 used an 18 gauge needle puncture, whereas the revised procedure used puncture holes ranging from 2.8 mm to 4 mm×6 mm).

In addition, a new vest was derived to directly measure adherence of the dressing to the injured tissue.

Example 1

In order to apply the haemostatic test articles to the surface of an injured artery surrounded by a tissue stimulant, the test articles were housed in cylindrical molds made of 10 or 3 mL polypropylene syringes (Becton Dickinson) with the luer-lock end removed. The plungers were withdrawn to the 6 mL and 2 mL mark respectively. For dressings utilizing a backing, the support material was cut and placed into each mold and pushed down until it was adjacent to the plunger. Once prepared the molds were placed upright and surrounded by dry ice, leaving the opening exposed at the top. 1 ml of fibrinogen and 0.15 mL of thrombin (with or without backing material dispersed within) were dispensed into the 10 mL molds and 1 ml of fibrinogen and 0.15 mL of thrombin (with or without support material dispersed within) were dispensed into the 3 mL molds, which were allowed to freeze for 5 minutes. The molds were then placed into the −80° C. freezer for at least two hours before being placed into a pre-cooled Genesis™ lyophylizer (Virtis, Gardiner, N.Y.). The chamber was sealed and the temperature equilibrated. The chamber was then evacuated and the dressings lyophilized via a primary and secondary drying cycle.

They were subsequently performance tested in a modified EVPA assay (Deep Tissue EVPA). Briefly, in one version, a plastic foam form was slipped over the artery. This covering had a hole in it that corresponded to the hole in the artery and the surrounding tissue (FIG. 1). In another variant, the foam was replaced with a piece of tissue, specifically, bovine muscle, in which a hole had been prepared as with the foam. The foam was maintained at 37° C. by placement in a 37° C. water bath, while the muscle tissue was maintained at 37° C. by placement on a 37° C. block heater. Warm saline was added to the surface of the dressing and the mold was immediately passed down thru the hole in the foam to the artery surface. The plunger was then depressed and held by hand for 3 minutes, after which the mold was withdrawn as the plunger was depressed further. At this point the artery was pressurized and the assay continued as described hereafter.

Deep Tissue EVPA Testing

Equipment and Supplies:

In-line high pressure transducer (Ashcroft Duralife™ or equivalent)

Peristaltic pump (Pharmacia Biotech™, Model P-1 or equivalent)

Voltmeter (Craftsman™ Professional Model 82324 or equivalent)

Computer equipped with software for recording pressure or voltage information

Tygon™ tubing (assorted sizes) with attachments

Water bath (Baxter Durabath™ or equivalent), preset to 37° C.

Incubation chamber (VWR™, Model 1400G or equivalent), preset to 37° C.

Thermometer to monitor temperatures of both water bath and oven

Assorted forceps, hemostats, and scissors 10 cc. and 20 cc. syringes with an approximately 0.6 cm hole drilled in center and smaller hole drilled through both syringe and plunger. This hole, drilled into the end of the syringe, will be used to keep the plunger drawn back and stationary.

O-rings (size 10 and 13)

Plastic Shields to fit the 10 cc and 20 cc syringes (approximately 3.5 cm in length)

P-1000 Pipetman™ with tips

Programmable Logic Controller (PLC) to control the pumps to maintain the desired pressure profile (Optional. Manual control may be used if desired.)

1. Materials and Chemicals

Porcine descending aortas (Pel-Freez Biologicals™, Catalog # 59402-2 or equivalent)

Cyanoacrylate glue (Vetbond™, 3M or equivalent)

18-gauge needle(s)

0.9% Saline, maintained at 37° C.

Red food coloring

Vascular Punch(es), 2.8 mm or other

Plastic Wrap

2. Artery Cleaning and Storage

1. Store arteries at −20° C. until used.
2. Thaw arteries at 37° C. in $H_2O$ bath.
3. Clean fat and connective tissue from exterior surface of artery.
4. Cut the arteries into ~5 cm segments.
5. The arteries may be refrozen to −20° C. and stored until use.

3. Artery Preparation for Assay

1. Turn the artery inside-out so that the smooth, interior wall is facing outwards.
2. Stretch a size 13 O-ring over a 20 cc syringe or a size 10 O-ring over a 10 cc syringe with an approximately 0.6 cm (0.25 in) hole drilled into one side.
3. Pull the artery onto the syringe, taking care not to tear the artery or have a too loose fit. The artery should fit snugly to the syringe. Slide another O-ring of the same size onto the bottom of the syringe
4. Carefully pull both O-rings over the ends of the artery. The distance between the O-rings should be at least 3.5 cm
5. Using the blade of some surgical scissors, gently scrape the surface of the artery in order to roughen the surface of the artery.
6. Use a 18-gauge needle to poke a hole through the artery over the site of the hole in the syringe barrel (see note above)
7. The tip of the biopsy punch is inserted through the hole in the artery. Depress the punch's plunger to make an open hole in the artery. Repeat a couple of times to ensure that the hole is open and free of connective tissue.
8. Patch holes left by collateral arteries. Generally this is done by cutting a patch from a latex glove and gluing it over the hole with cyanoacrylate glue. Allow the glue to cure for at least 10 minutes.

Place the artery in the warmed, moistened container and place in the incubation chamber. Allow the arteries to warm for at least 30 minutes.

4. Solution and Equipment Preparation

1. Check to see that the water bath, block heater and incubation chamber are maintained at 37° C.
2. Make sure that there is sufficient 0.9% saline in the pump's reservoir for completion of the day's assays. Add more if needed.
3. Place 0.9% saline and 0.9% saline with a few drops of red food coloring added into containers in a water bath so that the solutions will be warmed prior to performing the assay.
4. Prepare the container for warming the arteries in the incubation chamber by lining with KimWipes™ and adding a small amount of water to keep the arteries moist.
5. Check the tubing for air bubbles. If bubbles exist, turn on the pump and allow the 0.9% saline to flow until all bubbles are removed.

5. Application of the Dressing

1. Slip either the warmed (at 37° C. ) plastic foam form or the warmed tissue over the artery. Align the hole in it to correspond to the hole in the artery and the surrounding tissue (FIG. 1).
2. Open the haemostatic dressing (Test Article) pouch and remove haemostatic dressing & Applicator.
3. Slowly wet the haemostatic dressing drop wise with 0.9% saline warmed to 29-33° C. or other blood substitute, taking care to keep the saline from running off the edges. Any obvious differences in wetting characteristics from the positive control should be noted on the data collection forms.

NOTE: By way of example, a representative (13-15 mg/$cm^2$ of fibrinogen) 2.4×2.4 cm haemostatic dressing should generally be wet with 800 μl of saline or other blood substitute. The amount of saline used can be adjusted depending on the requirements of the particular experiment being performed; however, any changes should be noted on the data collection forms.

4. Immediately pass the dressing in the applicator down thru the hole in the foam to the artery surface. Depress the plunger by hand and hold by hand for 3 minutes, after which the applicator is withdrawn as the plunger was depressed further.
5. After polymerization, note the condition of the haemostatic dressing. Any variation from the positive control should be noted on the data collection form.

EXCLUSION CRITERION: The mesh support material must remain over the hole in the artery. If it has shifted during the polymerization and does not completely cover the hole the haemostatic dressing must be excluded.

Testing Procedure

1. Diagram of Testing Equipment Set-Up

The set-up of the testing equipment is shown in FIG. 1. Some additional, unshown components may be utilized to read out (pressure gauge) or control the pressure within the system 2. Equipment and Artery Assembly Fill the artery and syringe with red 0.9% saline warmed to 37° C., taking care to minimize the amount of air bubbles within the syringe and artery. Filling the artery with the opening uppermost can assist with this. Attach the artery and syringe to the testing apparatus, making sure that there are as few air bubbles in the tubing as possible. The peristaltic pump should be calibrated so that it delivers approximately 3 ml/min. If available, the PLC should be operated according to a pre-determined range of pressures and hold times as appropriate for the article being tested. If under manual control, the pressure/time profile to be followed is attained by manually turning the pump on and off while referencing the system pressure as read out by one or more pressure-reading components of the system. Following the conclusion of testing, the haemostatic dressing is subjectively assessed with regard to adhesion to the artery and formation of a plug in the artery hole. Any variations from the positive control should be noted on the data collection form.

Success Criteria

Haemostatic dressings that are able to withstand pressures for 3 minutes are considered to have passed the assay. When a haemostatic dressing has successfully passed the assay the data collection should be stopped immediately so that the natural decrease in pressure that occurs in the artery once the test is ended isn't included on the graphs. Should the operator fail to stop data collection, these points can be deleted from the data file to avoid confusing the natural pressure decay that occurs post-test with an actual dressing failure. The entire testing period from application of the haemostatic dressing to completion must fall within pre-established criteria. The maximum pressure reached should be recorded on the data collection form.

Failure Criteria

Haemostatic dressings that start leaking saline at any point during testing are considered to have reached the end of the assay.

NOTE: Build failures that are caused by artery swelling can be ignored and the test continued or re-started (as long as the total testing time doesn't fall beyond the established limit).

When leakage does occur, the pressure should be allowed to fall ~20 mmHg before data collection is stopped so that the failure is easily observed on the graphs. The pressures at which leakage occurred should be recorded on the data collection form. Should the data collection stop in the middle of the experiment due to equipment failure the data can be collected by hand at 5 second intervals until the end of the test or haemostatic dressing failure, whichever happens first. The data points should be recorded on the back of the data collection form, clearly labeled, and entered by hand into the data tables.

Exclusion Criteria

If the total testing period exceeds the maximum allowed for that procedure, regardless of cause, results must be excluded. If there are leaks from collaterals that can't be fixed either by patching or finger pressure the results must be excluded. If the test fails because of leaks at the O-rings, the results must be excluded. If the mesh support material does not completely cover the hole in the artery, the results must be excluded.

Adherence Performance Testing

Equipment and Supplies

Hemostat(s), Porcine artery and haemostatic dressing, optionally after performance of EVPA assay.

Preparation of the Artery+Dressing

After application of the dressing without completion of the EVPA Assay, the dressing is ready for the Adherence Assay and Weight Limit Test (if applicable). After application of the dressing and subsequent EVPA Analysis, the artery and syringe system is then disconnected slowly from the pump so that solution does not spray everywhere. The warmed, red saline solution from the EVPA Assay remains in the syringe until the Adherence Assay and Weight Limit Test (if applicable) is completed.

Performance of the Adherence Assay

1. After preparation of the artery and dressing (with or without EVPA analysis), gently lift the corner of the mesh and attach a hemostat of known mass to the corner.

NOTE: If the FD developed a channel leak during the performance of the EVPA Assay, test the adherence on the opposite of the haemostatic dressing to obtain a more accurate assessment of the overall adherence.

2. Gently let go of the hemostat, taking care not to allow the hemostat to drop or twist. Turn the syringe so that the hemostat is near the top and allow the hemostat to peel back the dressing as far as the dressing will permit. This usually occurs within 10 seconds. After the hemostat has stopped peeling back the dressing, rate the adherence of the bandage according to the following scale:

TABLE 1.1

| Dressing Performance Score | Amount of Adherence |
|---|---|
| 4 | 90+% |
| 3 | 75-90% |
| 2 | 50-75% |
| 1 | ~50% |
| 0.5 | Only the plug holds the hemostat |
| 0 | No adherence |

Exclusion Criteria

The mesh support material must remain over the hole in the artery. If it has shifted during the polymerization and does not completely cover the hole the haemostatic dressing must be excluded.

Success Criteria

Dressings that are given an adherence score of 3 are considered to have passed the assay.

Failure Criteria

If a dressing does not adhere to the artery after application and/or prior to performing the EVPA assay, it is given a score of 0 and fails the adherence test. If a dressing receives a score ≤2, the dressing is considered to have failed the Adherence Assay.

Weight Held Performance Assay

After the initial scoring of the "Adherence Test", weights may then be added to the hemostat in an incremental manner until the mesh support material is pulled entirely off of the artery. The maximum weight that the dressing holds is then recorded as a measure of the amount of weight the dressing could hold attached to the artery.

Example 2

Similar to the need to evaluate a test article in the context of sealing and injury deep within surrounding tissue, there was also a need to test products that can seal injured tissue where the injured vessels are smaller and thinner-walled than an aorta. The following assay accomplishes this goal.

According to this modification, the porcine carotid artery is attached to a barbed female connector using cotton thread with the connective tissue side exposed. This is in contrast to the standard EVPA where the internal side is exposed. As the carotid arteries used in the VA model are more elastic and friable than the aorta, it is more difficult to treat or abrade the surface without damaging and compromising the artery. To ensure that no tears have occurred during the removal of the bulk of the connective tissue, the artery is connected to the barbed connector and solution is pumped into it. If the artery is intact, a 1.5 mm hole is punched into the artery using a biopsy punch.

After the artery is prepped, it is connected to the pump system and placed on top of a piece of foam with a concave "hollow" cut into the surface. This serves as a support for the artery during application of the FD and "compression" of the artery. The test article is applied to the top of the hole and wet with 37° C. 0.9% NaCl. the artery is covered with plastic wrap, and a weight warmed to ~38-40° C. is then placed on top of the artery. The artery is partially compressed instead of being pressed flat because of the support of the foam.

After the weight has been applied for 5 min., it is then removed, and the pump is turned on. When the solution is coming out of the end of the artery, it is then clamped and allowed to pressurize until 250 mmHg or a leak occurs, whichever comes first.

In development of the assay, the following variables were considered and tested:

Tissue Selection: In order to mimic a vascular access procedure, a tissue substrate that was elastic yet strong was needed. Contact with rendering companies such as PelFreeze and Animal Technologies revealed 2 types of arteries collected that could be potentially used to mimic the vascular access procedure: porcine renal arteries and porcine carotid arteries. These arteries were comparable in size to a human femoral artery. Both types were purchased to examine their usefulness. The porcine renal artery was too short in useable length (less than 2"), to small an internal diameter, and not as elastic as desired. The porcine carotid artery, however, was highly elastic and offered useable segments of 3-5" without branching or collateral arteries.

Artery Hole Size: To determine a size to use for the assay, the actual surgical procedure was mimicked insofar as possible. A hole was put into the artery using an 18-gauge needle. A 200 uL pipette tip was then pushed into the hole to the point where the diameter was ~3.5 mm, just larger than a 10 F catheter. The tip was left in place for 2 hrs. and was then removed. The resulting hole was larger than the initial 18-gauge needle punch and, when compared to 2.8, 2.0, and 1.5 mm holes, was very similar to the 1.5 mm hole produced by the biopsy punch.

Surface Preparation: In the EVPA assay, the interior surface of a porcine aorta is gently abraded using the edge of a pair of scissors to provide a "damaged" surface to which the FD would adhere, mimicking large trauma. For the vascular access procedure, obtaining a uniform, reproducible surface on which to test the FD was important. Starting with the familiar, the carotid artery was turned inside-out and abraded. However, this did not work as the carotid artery is highly elastic, and the scraping of the surface created tears that rendered the artery unusable. Using the exterior surface, the arteries that had the connective tissue carefully removed down to the level of the artery provided a surface that was uniform and best mimicked the vascular access procedure.

Integration of the Artery into the Pump System: To best mimic the vascular access procedure, the use of the artery without any internal support to interfere with compression was desired. In order to incorporate the artery into the pump system, it was necessary to attach the artery at one end to the tubing and still have an open end to allow solution flow prior to pressurization. After examining different types of tubing and connectors, a barbed low-pressure female connector was chosen. The barb could be either ⅛" or ¼", depending upon the inner diameter of the carotid artery. To attach the artery to the barbed end, cable ties, o-rings, and thread were tested. Only the thread prevented leakage during pressurization.

Arterial Support: In trying to partially-compress the artery on a flat surface, it became clear that some form of support was needed to prevent the artery from shifting during application of the FD and to prevent total compression of the artery. A variety of materials were tested, including gel packs, Stytofoam packaging material, and foam pieces. Foam pieces that had a concave trough cut into the top surface offered the best support: the trough held the artery in place, and it was cut just deep enough to allow partial compression of the artery.

Compression Method: In the actual surgical procedure, hemostasis is more commonly achieved by manual compression of the artery for a period of ~20 min. During this time, arterial flow is maintained. Application of a weight to the artery was tested in order to mimic this at the lab bench. Various weights in beakers just large enough to contain the weight were tested on arteries in the foam arterial support. With this set-up, both 200 g and 500 g weight inside a glass beaker (to provide a uniform surface for compression) just large enough to accommodate the weight proved to be ideal for compression. Weights lower or higher provided insufficient or too much compression, respectively.

Temperature maintenance: FXIII, a component of the FD that is responsible for cross-linking of fibrin monomers, is thermally labile, and the assay needs maintained around normal body and wound temperatures of 34-36° C. As this set-up cannot be easily transferred to an incubator as in the EVPA, another method had to be devised. Various methods were considered such as warmed gel packs, heating pads, and warming lamps. While these methods would produce a warmer-than-ambient temperature, they were difficult to control to the level that this assay requires. The most practical method was the use of a heat block set to 37° C. While a heat block can maintain a constant temperature for very long periods of time, they were not sufficient to warm the artery and FD to 34-36° in the 5 minute time frame of the assay. As the weight that is applied could be a potential heat source, it was warmed in the incubator prior to application, and this addition to the 37° C. heat block was sufficient to maintain the 34-36° C. temperature range.

Data Collection: For this assay, the following pieces of data are collected: amount of saline required to wet the dressing, ease of wetting, artery temperature after the incubation period, maximum pressure obtained, failure mode (channel leak, leak through plug), qualitative assessment of the adherence of the dressing to the artery, and overall comments on dressing appearance (mottled, pre-formed fibrin, thin, etc.)

1 Test Protocol for Ex Vivo Porcine Carotid Artery Assay (EVPCA)

Equipment and Supplies

In-line high pressure transducer (Ashcroft Duralife or equivalent)

Peristaltic pump (Pharmacia Biotech, Model P-1 or equivalent)

Voltmeter (Craftsman Professional Model 82324 or equivalent)

Computer equipped with software for recording pressure or voltage information

Tygon tubing (asst. sizes) with attachments

Water bath (Baxter Durabath or equivalent), preset to 37° C.

Heat Block (Thermolyne Type 16500 Dri-Bath or equivalent)

Incubation chamber (VWR, Model 1400G or equivalent), preset to ~40° C.

Thermometer to monitor temperatures of water bath, heat block, and oven

Calibration weights: 200 g and 500 g

Beakers to hold calibration weights

Biopsy punch(es), 1.5 mm or other required sizes

Assorted forceps, hemostats, and scissors

P-200 and P-100 Pipetman with tips

Plastic ⅛" and ¼" low pressure fittings, female connector with a barbed tubing connection Plastic strips ⅛" and ¼" wide Materials and Chemicals Porcine carotid arteries (xxx or equivalent)

0.9% Saline, maintained at 37° C.

Red food coloring

Quilting thread or other heavy-gauge thread

Plastic Wrap

Foam pieces with a concave area cut into the surface

Preliminary Procedures

Artery Cleaning and Storage

1. Store arteries at −20° C. until used.

2. Thaw arteries at 37° C. in $H_2O$ bath.

3. Clean fat and connective tissue from exterior surface of artery.

4. The arteries may be refrozen to −20° C. and stored until use.

Artery Preparation for Assay

1. Make sure that all connective tissue is removed from the artery.

2. If any collateral arteries or other large holes are visible, cut the artery at the hole. If a small section of artery is produced from the cut, discard it. If 2 pieces are produced that are at least 1½" long, both pieces may be used for assays.

3. Insert the barbed end of a low pressure connector, either ⅛" or ¼" depending upon the internal diameter of the artery, into the larger end of the artery.

4. Cut a piece of quilting or other heavy thread ~6" long. Using a square knot, tie the artery to the connector so that it does not come off of the connector.

Note: As it is possible to tear the artery during the cleaning process, it is important to "leak test" the artery prior to performing the assay.

5. Connect the artery to the male connector at the end of the tubing attached to the pump system.

6. Turn on the pump with the open end of the artery pointed upwards and allow the artery to fill with the red 0.9% NaCl. When the artery is full, clamp the artery closed using a hemostat.

7. Watch the artery as it pressurizes to see if any holes or tears are present. If a hole is present, turn off the pump, unclamp the artery over a beaker to catch the saline solution, and disconnect it from the pump system.

For Arteries With Holes

If the hole is near the open end of the artery, cut off the artery at the hole, leaving the artery attached to the connector.

If the hole is near the connector, remove the artery from the connector, cut the artery at the hole, and re-attach it to the connector as outlined above.

For arteries that have pieces cut off, the remaining piece should be at least 1½" long. If not, it should be discarded.

If the hole is near the middle of the artery, check the size of the hole. If it is less than 1.5 mm, it may be used for the assay as a hole may be punched around it. If the hole is larger than 1.5 mm, the artery should be discarded.

For Arteries Without Holes

If no holes are seen, allow the artery to pressurize to ~00 mmHg (a reading of 2.0 on the pressure gauge). Turn off the pump and unclamp the artery over a beaker, and disconnect it from the pump system.

If any holes become visible during this period, unclamp the artery over a beaker, disconnect form the pump system, and fix the artery according to the procedures outlined above.

Note: After the artery has been inspected and any unwanted holes addressed, the test hole may then be punched in the artery 8. Insert a plastic strip into the open end of the artery so that it goes most of the way into the artery.

9. Using the biopsy punch, carefully punch a hole in the artery. Make sure that the punch connects with the plastic strip so that no additional holes are punched in the artery.

10. The punch should totally remove the center portion. If it does not, gently remove it with forceps or by re-cutting it using the biopsy punch.

11. Place the artery in the warmed, moistened container and place in the ~40° C. incubation chamber to keep the artery moist prior to assay Solution and Equipment Preparation 1. Turn on the heat block and check to see that it is maintained at 37° C.

2. Check to see that the water bath is maintained at 37° C. and incubation chamber is maintained at ~40° C.

3. Make sure that there is sufficient 0.9% saline in the pump's reservoir for completion of the day's assays. Add more if needed.

4. Place 0.9% saline into containers in a 37° C. water bath so that the solutions will be warmed prior to performing the assay.

5. The peristaltic pump should be calibrated so that it delivers approximately 3 ml/min. If not, adjust the settings at this point.

6. Check the tubing for air bubbles. If bubbles exist, turn on the pump and allow the 0.9% saline to flow until all bubbles are removed.

Application of the FD or HD

1. Place a piece of foam with the concave surface on top of the heating block and cover with a piece of plastic wrap.

2. Remove an artery from the warming box and attach it to the pump system.

3. Allow the artery to rest in the concave hollow of the foam piece.

4. Open the haemostatic dressing pouch and remove haemostatic dressing(s). Place any extras in the vacuum dessicator.

5. Place the dressing, mesh support material side UP (or the side closest to the bottom of the mold if no support material is present), over the hole in the artery 6. Slowly wet the haemostatic dressing with an amount of saline appropriate for the article being tested NOTE: A standard (13-15 mg/cm$^2$ of fibrinogen) 2.4×2.4 cm haemostatic dressing should be wet with 800 μl of saline or other blood substitute. A dressing of 1.5×1.5 cm would require 300 μl of saline or other blood substitute, and a 0.7×0.7 cm dressing would require 70 μl of saline or other blood substitute. The amount of saline used can be adjusted depending on the requirements of the particular experiment being performed, however, any changes should be noted on the data collection forms.

NOTE: Wet the haemostatic dressing drop wise with 0.9% saline warmed to 37° C. or other blood substitute, taking care to keep the saline from running off the edges. Any obvious differences in wetting characteristics from the positive control should be noted on data collection forms.

7. Cover the artery with plastic wrap, taking care that the dressing doesn't slide around on the surface of the artery.

8. Place a warmed weight carefully on top of the dressing so that it does not shift off of the hole in the artery.

9. Allow the weight to remain on the artery on top of the 37° C. heat block for the duration of the polymerization time.

NOTE: Time, pressure, and hole size can be altered according to the requirements of the experiment; changes from the standard conditions should be noted on the data collection forms.

10. After polymerization, carefully unwrap the artery and note the condition of the haemostatic dressing. Any variation from the positive control should be noted on the data collection form.

EXCLUSION CRITERION: The mesh support material must remain over the hole in the artery. If it has shitted during the polymerization and does not completely cover the hole the haemostatic dressing must be excluded.

Testing Procedure

A diagram of testing equipment set-up is shown in FIG. 1.

TABLE 2.1

Conversion Table for Pressure (PSI) to mmHg and Voltage

| Pressure Gauge Reading (PSI) | mm Hg Equivalent | Voltage Equivalent |
|---|---|---|
| 1.0 | 50 | 1.25 |
| 2.0 | 100 | 1.50 |
| 3.0 | 150 | 1.75 |
| 4.0 | 200 | 2.00 |
| 5.0 | 250 | 2.25 |

Equipment and Artery Assembly

1. After the polymerization period is complete, carefully remove the plastic wrap so that the dressing is not disturbed.

2. Turn on the pump and gently lift the open end of the artery with a hemostat. Allow the artery to fill to the top with 0.9% NaCl. This is done to minimize air bubbles in the system.

3. The system should be operated according to a pre-determined range of pressures and hold times as appropriate for the article being tested. Should the pressure drop below the desired maximum during the hold period, the pump should be turned on again until the maximum pressure is achieved.

4. Should a leak in the system develop other than failure of the FD or HD (i.e. leaking from a hole in the artery, etc.), attempts to correct the problem should be taken. This might involve clamping the leak for the remainder of the assay. Should the attempts to fix the problem be ineffective, the test article will be excluded from analysis and called a "system failure" (See Exclusion Criteria below).

5. Following the conclusion of testing, the haemostatic dressing is subjectively assessed with regard to adhesion to the artery and formation of a plug in the artery hole. Any variations from the positive control should be noted on the data collection form.

Success/Fail and Exclusion Criteria

Success Criteria

1. Haemostatic dressings that are able to withstand various pressures for 3 minutes are considered to have passed the assay.

2. When a haemostatic dressing has successfully passed the assay the data collection should be stopped immediately so that the natural decrease in pressure that occurs in the artery once the test is ended isn't included on the graphs. Should the operator fail to stop data collection, these points can be deleted from the data file to avoid confusing the natural pressure decay that occurs post-test with an actual dressing failure.

3. The entire testing period from application of the haemostatic dressing to completion must fall within pre-established criteria.

NOTE: For a single-step increase to maximum pressure the entire testing period should not exceed 15 minutes. Other time limits may be established for other test procedures, and should be noted on the data collection forms.

4. The maximum pressure reached should be recorded on the data collection form.

NOTE: Typical challenge is 250 mmHg for three minutes in one step, but that may be altered based on the article being tested. The pressure, for example, may be increased in "steps" with holds at various pressures until the 250 mmHg is achieved. One example is increasing the pressure in 50 mmHg increments with a 1 minute hold at each step to ensure that the FD or HD can hold these pressure.

Failure Criteria

1. Haemostatic dressings that start leaking saline at the point of FD or HD attachment at any point during testing are considered to have failed the assay.

NOTE: Build failures that are caused by artery swelling can be ignored and the test continued or re-started (as long as the total testing time doesn't fall beyond the established limit).

2. When leakage from the FD or HD does occur, the pressure should be allowed to fall ~20 mmHg before data collection is stopped so that the failure is easily observed on the graphs.

3. The pressures at which leakage occurred should be recorded on the data collection form.

4. Should the data collection stop in the middle of the experiment due to equipment failure the data can be collected by hand at 5 second intervals until the end of the test or haemostatic dressing failure, whichever happens first. The data points should be recorded on the back of the data collection form, clearly labeled, and entered by hand into the data tables.

Exclusion Criteria

1. If the total testing period exceeds the maximum allowed for that procedure, regardless of cause, results must be excluded.

2. If there are leaks from holes that can't be fixed by clamping or finger pressure the results must be excluded.

3. If the mesh support material does not completely cover the hole in the artery, the results must be excluded Example 3

For all dressings, ERL fibrinogen lot 3130 was formulated in CFB. The final pH of the fibrinogen was 7.4±0.1. The fibrinogen concentration was adjusted to 37.5 mg/ml. Once prepared the fibrinogen was placed on ice until use. Thrombin was formulated in CTB. The final pH of the thrombin was 7.4±0.1. The thrombin was adjusted to deliver 0.1 units/mg of Fibrinogen or 25 Units/ml thrombin. For the group with shredded support material dispersed within, it was cut into approximately 1 mm×1 mm pieces and dispersed within the thrombin solution prior to filling the molds. Once prepared the thrombin was placed on ice until use. The temperature of the fibrinogen and thrombin prior to dispensing was 4° C.±2° C. Cylindrical molds made of 10 or 3 mL polypropylene syringes (Becton Dickinson) with the luer-lock end removed were used. The plungers were withdrawn to the 6 mL and 2 mL mark respectively. For dressings utilizing a support material, the support material was cut and placed into each mold and pushed down until it was adjacent to the plunger. Once prepared the molds were placed upright and surrounded by dry ice, leaving the opening exposed at the top. 1 ml of fibrinogen and 0.15 mL of thrombin (with or without support material dispersed within) were dispensed into the 10 mL molds and 1 ml of fibrinogen and 0.15 mL of thrombin (with or without support material dispersed within) were dispensed into the 3 mL molds, which were allowed to freeze for 5 minutes. The molds were then placed into the −80° C. freezer for at least two hours before being placed into the freeze dryer and lyophylized as described above. The compositions are shown in Table 3.1 below.

TABLE 3.1

| Mold Size | Fibrinogen Dose (mg/cm$^2$) | Thrombin Dose (U/cm$^2$) | T:F Ratio |
|---|---|---|---|
| 3 ml | 75 | 7.5 | 0.1 |
| 10 ml | 25 | 2.5 | 0.1 |

Upon removal from the lyophylizer, both groups were performance tested in a modified EVPA assay as described in Example 1 above. Briefly, a plastic foam form was slipped over the artery. This covering had a hole in it that corresponded to the hole in the artery and the surrounding tissue. Warm saline was added to the surface of the dressing and the mold was immediately passed down thru the hole in the foam to the artery surface. The plunger was then depressed and held by hand for 3 minutes, after which the mold was withdrawn as the plunger was depressed further. At this point the artery was pressurized and the assay continued as described in Example 1 above.

Results

TABLE 3.1

| Support Material | Mold Size | EVPA Result (@250 mmHg) | Maximum Pressure |
|---|---|---|---|
| None | 10 ml | Pass | >250 mmHg |
| Dexon Mesh Backing | 10 ml | Pass | " |
| " | 3 ml | Pass | " |
| Shredded Dexon Mesh (Dispersed) | 10 ml | Pass | " |
| Shredded Dexon Mesh (Dispersed) | 3 ml | Fail | 150 mm Hg |

Conclusions: Dressings that included no support material or a DEXON™ mesh support material performed well, with all passing the EVPA test at 250 mmHg. When the support material was dispersed throughout the composition, the dressings also performed well, with the large size (10 mL mold) dressings holding the full 250 mmHg of pressure, while the smaller held up to 150 mmHg of pressure. This indicates that the use of a support material may be optional, and it's location may be on the 'back' of the dressing, or dispersed throughout the composition, as desired.

The results demonstrate that the dressings were effective at the highest pressure tested regardless of size, and that they functioned effectively regardless of the presence or absence of the support material. Higher performance was associated with the presence of support material, and a larger applicator.

Example 4

Dexon™ Mesh support material was cut to fit into and placed into each PETG 1.5×1.5 cm mold. Fifteen microliters of 2% sucrose was pipeted on top of each of the four corners of the support material and the molds were placed inside a −80° C. freezer. Once completed the molds were placed in a −80° C. freezer. All molds remained in the −80° C. freezer for at least 60 minutes. Enzyme Research Laboratories (ERL) Fibrinogen lot 3150 was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 37.5 mg/ml. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4+/−0.1. The thrombin was adjusted to 25 Units/ml thrombin, resulting in 0.1 units/mg of Fibrinogen or 1.3 U/cm$^2$. Once prepared the thrombin was placed on ice until use. The temperature of the fibrinogen and thrombin prior to dispensing was 4° C.+/−2° C. Molds were removed from the −80° C. freezer and placed on a copper plate that was placed on top of dry ice. A repeat pipetor was filled with fibrinogen and second repeat pipetor was filled with thrombin. Simultaneously 0.8 ml of fibrinogen and 133 micro liters of thrombin were dispensed into each mold. Once the molds were filled, they were returned to the −80° C. freezer for at least two hours before being placed into a pre-cooled Genesis™ lyophylizer (Virtis, Gardiner, N.Y.). The chamber was sealed and the temperature equilibrated. The chamber was then evacuated and the dressings lyophilized as described in Example 3.

Test articles of a different size were also prepared as follows. Support material was cut and placed into each PETG 0.7×0.7 cm mold. Five microliters of 2% sucrose was pipeted on top of each of the four corners of the support material and the molds were placed inside a −80° C. freezer. Once completed the molds were placed in a −80° C. freezer. All molds remained in the −80° C. freezer for at least 60 minutes. Enzyme Research Laboratories (ERL) Fibrinogen lot 3150 was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 39.2 mg/ml. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4+/−0.1. The thrombin was adjusted to 25 Units/ml thrombin, which resulted in a final composition of 0.1 units/mg of Fibrinogen or 1.3 U thrombin/cm$^2$. Once prepared the thrombin was placed on ice until use. The temperature of the fibrinogen and thrombin prior to dispensing was 4° C.+/−2° C. Molds were removed from the −80° C. freezer and placed on a copper plate that was placed on top of dry ice. A repeat pipetor was filled with fibrinogen and second repeat pipetor was filled with thrombin. Simultaneously 0.17 ml of fibrinogen and 26 micro liters of thrombin were dispensed into each mold. Once the molds were filled, they were returned to the −80° C. freezer for at least two hours before being placed into the freeze dryer and lyophylized as described above.

The performance of the test articles was determined using the EVPCA assay as described in Example 2 above.

Results:

TABLE 4.1

| Test Article Size (cm$^2$) | Fibrinogen Dose (mg/cm$^2$) | Thrombin Dose (U/cm$^2$) | T:F (U/mg) | % Reaching 100 mmHg | % Reaching 150 mmHg | % Reaching 200 mmHg | % Reaching 250 mmHg |
|---|---|---|---|---|---|---|---|
| 0.7 | 13 | 1.3 | 0.1 | 100 | 80 | 40 | 40 |
| 1.5 | 13 | 1.3 | 0.1 | 100 | 80 | 80 | 60 |

Example 5

Dexon™ Mesh support material was cut to fit into and placed into each PETG 1.5×1.5 cm mold. Fifteen microliters of 2% sucrose was pipeted on top of each of the four corners of the support material and the molds were placed inside a −80° C. freezer. PETG 1.5×1.5 cm molds that did not contain support material were also placed inside the −80° C. freezer. In a third group, the same amount of support material was cut into small pieces (approximately less than 2 mm×2 mm) and placed into PETG 1.5×1.5 cm molds (these dressings are referred to as having their support material 'dispersed'). Once completed the molds were placed in a −80° C. freezer. All molds remained in the −80° C. freezer for at least 60 minutes. Enzyme Research Laboratories (ERL) Fibrinogen lot 3130 was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 36.56 mg/ml and 14.06 mg/ml. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4+/−0.1. The thrombin was adjusted to deliver 0.01, 0.1 or 1 units/mg of Fibrinogen or 2.5, 25 or 250 Units/ml thrombin. Once prepared the thrombin was placed on ice until use. The temperature of the fibrinogen and thrombin prior to dispensing was 4° C.+/−2° C. Molds were removed from the −80° C. freezer and placed on a copper plate that was placed on top of dry ice. A repeat pipetor was filled with fibrinogen and second repeat pipetor was filled with thrombin. Simultaneously 0.8 ml of fibrinogen and 133 micro liters of thrombin were dispensed into each mold. Once the molds were filled, they were returned to the −80° C. freezer for at least two hours before being placed into the freeze dryer. Table 5.1 shows the experimental design.

TABLE 5.1

Experimental Design

| Fibrinogen Dose (mg/cm²) | Thrombin Dose (U/cm²) | T:F (U/mg) | Support material |
|---|---|---|---|
| 5 | 0.05 | 0.01 | Yes |
| 5 | 0.05 | 0.01 | No |
| 5 | 0.05 | 0.01 | Dispersed |
| 5 | 0.5 | 0.1 | Yes |
| 5 | 0.5 | 0.1 | No |
| 5 | 0.5 | 0.1 | Dispersed |
| 5 | 5 | 1 | Yes |
| 5 | 5 | 1 | No |
| 5 | 5 | 1 | Dispersed |
| 13 | 0.13 | 0.01 | Yes |
| 13 | 0.13 | 0.01 | No |
| 13 | 0.13 | 0.01 | Dispersed |
| 13 | 1.3 | 0.1 | Yes |
| 13 | 1.3 | 0.1 | No |
| 13 | 1.3 | 0.1 | Dispersed |
| 13 | 13 | 1 | Yes |
| 13 | 13 | 1 | No |
| 13 | 13 | 1 | Dispersed |

The performance of the test articles was determined using the EVPCA assay as described in Example 2 above.

Results:

TABLE 5.2

| Fibrinogen Dose (mg/cm²) | Thrombin Dose (U/cm²) | Thrombin (U/mg fibrinogen) | Support material | % Reaching 150 | % Reaching 200 | % Reaching 250 |
|---|---|---|---|---|---|---|
| 5 | 0.05 | 0.01 | Yes | 66.6 | 50 | 50 |
| 5 | 0.05 | 0.01 | No | 0 | 16 | 0 |
| 5 | 0.05 | 0.01 | Dispersed | 13.3 | 0 | 0 |
| 5 | 0.5 | 0.1 | Yes | 66.6 | 66 | 50 |
| 5 | 0.5 | 0.1 | No | 60 | 20 | 0 |
| 5 | 0.5 | 0.1 | Dispersed | 40 | 0 | 0 |
| 5 | 5 | 1 | Yes | 33.3 | 0 | 0 |
| 5 | 5 | 1 | No | 0 | 0 | 0 |
| 5 | 5 | 1 | Dispersed | 0 | 0 | 0 |
| 13 | 0.13 | 0.01 | Yes | 100 | 50 | 33.3 |
| 13 | 0.13 | 0.01 | No | 33.3 | 0 | 0 |
| 13 | 0.13 | 0.01 | Dispersed | 20 | 20 | 0 |
| 13 | 1.3 | 0.1 | Yes | 66.6 | 50 | 16.6 |
| 13 | 1.3 | 0.1 | No | 0 | 0 | 0 |
| 13 | 1.3 | 0.1 | Dispersed | 100 | 80 | 40 |
| 13 | 13 | 1 | Yes | 33.3 | 33.3 | 33.3 |
| 13 | 13 | 1 | No | 33.3 | 0 | 0 |
| 13 | 13 | 1 | Dispersed | 33.3 | 16.6 | 16.6 |

Example 6

Dexon™ Mesh support material was cut to fit into and placed into each PETG 0.7×0.7 cm mold. Five microliters of 2% sucrose was pipeted on top of each of the four corners of the support material and the molds were placed inside a −80° C. freezer. Once completed the molds were placed in a −80° C. freezer. All molds remained in the −80° C. freezer for at least 60 minutes. Enzyme Research Laboratories (ERL) Fibrinogen lot 3130 was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 39.2 mg/ml and 32.06 mg/ml. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4+/−0.1. The thrombin was adjusted to deliver 1 unit/mg of Fibrinogen or 250 Units/ml thrombin. Once prepared the thrombin was placed on ice until use. The temperature of the fibrinogen and thrombin prior to dispensing was 4° C.+/−2° C. Molds were removed from the −80° C. freezer and placed on a copper plate that was placed on top of dry ice. A repeat pipetor was filled with fibrinogen and second repeat pipetor was filled with thrombin. Simultaneously 0.2 ml of fibrinogen and 33 micro liters of thrombin were dispensed into each mold. Once the molds were filled, they were returned to the −80° C. freezer for at least two hours before being placed into the freeze dryer. Table 6.1 shows the experimental design.

TABLE 6.1

Experimental Design

| Fibrinogen Dose (mg/cm²) | Thrombin Dose (U/cm²) | T:F (U/mg) | Support material |
|---|---|---|---|
| 16 | 16.1 | 1 | Yes |
| 13 | 13.0 | 1 | Yes |

The performance of the test articles was determined using the EVPCA assay as described in Example 2 above.
Results:

TABLE 6.2

| Fibrinogen Dose (mg/cm²) | % Pass EVCPA at 150 mm Hg | % Pass EVCPA at 200 mm Hg | % Pass EVCPA at 250 mm Hg |
| --- | --- | --- | --- |
| 16 | 66.6 | 33.3 | 16.6 |
| 13 | 0 | 0 | 0 |

Example 7

Dexon™ Mesh support material was cut to fit into and placed into each PETG 1.5×1.5 cm mold. Fifteen microliters of 2% sucrose was pipetted on top of each of the four corners of the support material and the molds were placed inside a −80° C. freezer. Once completed the molds were placed in a −80° C. freezer. All molds remained in the −80° C. freezer for at least 60 minutes. Enzyme Research Laboratories (ERL) Fibrinogen lot 3170P was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 36.56 mg/ml and 14.06 mg/ml. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4+/−0.1. The thrombin was adjusted to deliver 0.001, or 0.0001 units/mg of Fibrinogen or 0.25, 0.025 Units/ml thrombin. Once prepared the thrombin was placed on ice until use. The temperature of the fibrinogen and thrombin prior to dispensing was 4° C.+/−2° C. Molds were removed from the −80° C. freezer and placed on a copper plate that was placed on top of dry ice. A repeat pipetor was filled with fibrinogen and second repeat pipetor was filled with thrombin. Simultaneously 0.8 ml of fibrinogen and 133 micro liters of thrombin were dispensed into each mold. Once the molds were filled, they were returned to the −80° C. freezer for at least two hours before being placed into the freeze dryer. Table 7.1 shows the experimental design.

TABLE 7.1

| Experimental Design | | | |
| --- | --- | --- | --- |
| Fibrinogen Dose (mg/cm2) | Thrombin Dose (U/cm²) | T:F (U/mg) | Support material |
| 13 | 0.013 | 0.001 | Yes |
| 13 | 0.0013 | 0.0001 | Yes |
| 5 | 0.005 | 0.001 | Yes |
| 5 | 0.0005 | 0.0001 | Yes |

The performance of the test articles was determined using the EVPCA assay as described in Example 2 above.

Example 8

Previously manufactured lyophylized mixtures of fibrinogen & thrombin (lot # 012408) were placed into a grinder (Krups) and ground (5 seconds) into a powder. The powdered dressings were placed into a 50 ml conical centrifuge tube. Twenty-five grams of sucrose was ground into powder and placed into another 50 ml conical centrifuge tube. Table 8.1 shows the design of the experiment.

TABLE 8.1

| Experimental Design | | | | | |
| --- | --- | --- | --- | --- | --- |
| Fibrinogen Dose (mg/cm²) | Thrombin Dose (U/cm²) | T:F (U/mg) | Support material/ Placement | Weight of Dressing Powder (g) | Weight of Sucrose (g) |
| 5 | 1.3 | 0.26 | Yes | 0.008 | 0.092 |
| 13 | 1.3 | 0.1 | Yes/Bottom | 0.208 | 0.792 |
| 13 | 1.3 | 0.1 | Yes/Top | 0.208 | 0.792 |
| 26 | 1.3 | 0.05 | Yes/Bottom | 0.416 | 0.584 |
| 26 | 1.3 | 0.05 | Yes/Top | 0.416 | 0.584 |
| 26 | 1.3 | 0.05 | Yes/Middle | 0.416 | 0.584 |
| 56 | 1.3 | 0.023 | Yes/Top | 0.12 | 0.00 |
| 56 | 1.3 | 0.023 | Yes/Middle | 0.12 | 0.00 |
| 450 | 1.3 | 0.003 | Yes/Middle | 0.95 | 0.00 |
| 5 | 1.3 | 0.26 | No | 0.008 | 0.092 |
| 13 | 1.3 | 0.1 | No | 0.208 | 0.792 |
| 26 | 1.3 | 0.05 | No | 0.416 | 0.584 |
| 56 | 1.3 | 0.023 | No | 0.12 | 0.00 |
| 5 | 1.3 | 0.26 | Dispersed | 0.008 | 0.092 |
| 13 | 1.3 | 0.1 | Dispersed | 0.208 | 0.792 |
| 26 | 1.3 | 0.05 | Dispersed | 0.416 | 0.584 |
| 56 | 1.3 | 0.023 | Dispersed | 0.12 | 0.00 |

For each group 0.1 g of the powder/sucrose was weighed and placed into a Carver 13 mm Evacuable Pellet Die. For pellets that had a support material, 75 mg of the support material was placed in one of four locations. In the first, the support material (Dexon™ mesh) was placed into the die, followed by the addition of the powder, these are referred to as being in the 'bottom' position. When the powder was placed into the die followed by the support material (Dexon™ mesh) these are referred to as in the 'top' position. For pellets with the support material in the 'middle' position, 50 mg of the powder/sucrose was weighed and placed into a Carver 13 mm Evacuable Pellet Die, followed by the support material (75 mg of Dexon™ mesh) which was then topped off by another 50 mg of the powder/sucrose mixture. For pellets that had dispersed support material, the powder and 75 mg of shredded support material (Dexon™ mesh) were added to the die at the same time and mixed for 5 seconds with a pipette tip. Once the die was filled with the appropriate material, it was placed in a Carver 4330 manual pellet press. Pressure was applied to give an applied load of 1000 lbs. The resulting pellets were removed and placed into a desiccator until tested.

The performance of the test articles was determined using the EVPCA assay as described in Example 2 above. The test articles containing a fibrinogen dose of 26 or 56 mg/cm² exhibited the best results.

Example 9

Previously manufactured lyophylized mixtures of fibrinogen & thrombin were placed into a grinder (Krups) and ground (5 seconds) into a powder. The powdered dressings were placed into a 5 0ml conical centrifuge tube. Twenty-five grams of sucrose was ground into powder and placed into another 50 ml conical centrifuge tube. Cylindrical molds made of 3 mL polypropylene syringes (Becton Dickinson) with the luer-lock end removed were used. The plungers were withdrawn to the 2 or 3 ml mark.

TABLE 9.1

Experimental Design

| Fibrinogen Dose (mg/cm$^2$) | Thrombin Dose (U/cm$^2$) | T:F (U/mg) | Support material | Weight of Dressing Powder (g) | Weight of Sucrose (g) |
|---|---|---|---|---|---|
| 26 | 1.3 | 0.05 | No | .0208 | 0.0792 |
| 26 | 1.3 | 0.05 | Yes | .0208 | 0.0792 |
| 26 | 1.3 | 0.05 | Dispersed | .0208 | 0.0792 |
| 56 | 1.3 | 0.023 | No | 0.0448 | 0.0552 |
| 56 | 1.3 | 0.023 | Yes | 0.0448 | 0.0552 |
| 56 | 1.3 | 0.023 | Dispersed | 0.0448 | 0.0552 |
| 150 | 1.3 | 0.0087 | No | 0.12 | 0.0 |
| 150 | 1.3 | 0.0087 | Yes | 0.12 | 0.0 |
| 150 | 1.3 | 0.0087 | Dispersed | 0.12 | 0.0 |
| 450 | 1.3 | 0.003 | No | 0.36 | 0.0 |
| 450 | 1.3 | 0.003 | Yes | 0.36 | 0.0 |
| 450 | 1.3 | 0.003 | Dispersed | 0.36 | 0.0 |

For dressings utilizing a support material, 75 mg of Dexon mesh support material was cut to fit into the mold and then placed into each mold and pushed down until it was adjacent to the plunger. Where syringes had dispersed support material, an equivalent amount of support material was shredded and dispersed within the powder that was added to each syringe. For each group 0.1 g of the powder/sucrose was weighed and placed into a each syringe, except for the 150 mg/cm$^2$ group which had 0.12 g added to the syringe. Gelfoam™ was cut to fit into the mold and then placed inside the syringes, either alone or with 26 mg/cm$^2$ of dressing powder.

The performance of the test articles was determined using the EVPCA assay as described in Example 2 above. The results are shown in Table 9.2 below.

Results:

TABLE 9.2

| Fibrinogen Dose (mg/cm$^2$) | Support Material | % Reaching 60 mmHg | % Reaching 100 mmHg | % Reaching 150 mmHg | % Reaching 200 mmHg | % Reaching 250 mmHg |
|---|---|---|---|---|---|---|
| 26 | Yes | 100 | 100 | 0 | 0 | 0 |
| 26 | Dispersed | 0 | 0 | 0 | 0 | 0 |
| 26 | No | 0 | 0 | 0 | 0 | 0 |
| 26 | Gelfoam ™ | 100 | 0 | 0 | 0 | 0 |
| 56 | Yes | 100 | 100 | 100 | 100 | 100 |
| 56 | Dispersed | 100 | 100 | 100 | 100 | 100 |
| 56 | No | 0 | 0 | 0 | 0 | 0 |
| 150 | Yes | 100 | 100 | 100 | 100 | 50 |
| 150 | Dispersed | 100 | 100 | 100 | 50 | 50 |
| 150 | No | 100 | 100 | 100 | 100 | 100 |
| 450 | Yes | 100 | 100 | 100 | 100 | 0 |
| 450 | Dispersed | 100 | 100 | 100 | 100 | 100 |
| 450 | No | 100 | 100 | 100 | 0 | 0 |

Example 10

Enzyme Research Laboratories (ERL) Fibrinogen lot 3170P was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 37.5 mg/ml. Once prepared the fibrinogen was placed on ice until use. Fibrinogen was diluted to 18.75 mg/ml and 9.4 mg/ml with Fibrinogen complete buffer.

Enzyme Research Laboratories (ERL) Fibrinogen lot 3170P was formulated in 100 mM Sodium Chloride, 1.1 mM Calcium Chloride, 10 mM Tris, 10 mM Sodium Citrate, and 1.5% Sucrose (Fibrinogen complete buffer). This group did not contain Sucrose or Tween. The final pH of the fibrinogen was 7.4+/−0.1. The fibrinogen concentration was adjusted to 37.5 mg/ml. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4+/−0.1. The thrombin was adjusted to deliver 0.1 units/mg of Fibrinogen or 25 Units/ml thrombin. Thrombin was diluted to 12.5 U/ml and 6.25 U/ml with Thrombin buffer. Once prepared the thrombin was placed on ice until use. The temperature of the fibrinogen and thrombin prior to dispensing was 4° C.+/−2° C. Microcentrifuge tubes (0.65 ml) were placed on dry ice. There were two groups of frozen plugs prepared with one frozen plug per group. One group did not have any support material, and the second group contained shredded support material (Dexon mesh) (0.1 g) dispersed within it. A repeat pipetor was filled with fibrinogen and second repeat pipetor was filled with thrombin. Simultaneously 0.5 ml of fibrinogen and 75 micro liters of thrombin were dispensed into each microcentrifuge tube. Once each microcentrifuge tube was filled, they were transferred to a −80° C. freezer until tested. Table 10.1 shows the experimental design.

TABLE 10.1

Experimental Design

| Fibrinogen Dose (mg/Item) | Thrombin Dose U/Item | T:F U/mg | Support Material |
|---|---|---|---|
| 18.75 | 1.875 | 0.1 | Dispersed |
| No Sucrose or Tween | | | |
| 18.75 | 1.875 | 0.1 | No |
| No Sucrose or Tween | | | |
| 18.75 | 1.875 | 0.1 | Dispersed |
| 18.75 | 1.875 | 0.1 | No |
| 9.4 | 0.94 | 0.1 | Dispersed |
| 9.4 | 0.94 | 0.1 | No |
| 4.7 | 0.47 | 0.1 | Dispersed |
| 4.7 | 0.47 | 0.1 | No |

The performance of the test articles was determined using a modified EVPCA assay. The EVPCA assay (described in Example 2 above) was modified to further enhance the faithfulness of the assay to the actual conditions that may be encountered in vivo. As described in Example 3, the surrounding of the test blood vessel by closely fitting material can replicate the use of these inventions in sealing an injury deep inside tissue. To further enhance this replication of such a clinical setting, tissue was substituted for the plastic foam that was wrapped around the vessel. The tissue may be chosen to best replicate the intended anatomical location. In this Example commercial meat was used to simulate the leg muscle of a patient undergoing a vascular access procedure. Sufficient tissue was used to simulate a depth of several inches of muscle tissue. Other than this modification, and the employment of an application device as described in Example #3, the assay was carried out as described in Example #2. The results are shown in Table 10.2 below.

Results:

TABLE 10.2

| Fibrinogen Dose (mg/Item) | Thrombin Dose (U/Item) | T:F U/mg | Support Material | % Reaching 100 mmHg | % Reaching 150 mmHg | % Reaching 200 mmHg | % Reaching 250 mmHg |
|---|---|---|---|---|---|---|---|
| 18.75 No Sucrose or Tween | 1.875 | 0.1 | Dispersed | 50 | 50 | 50 | 50 |
| 18.75 No Sucrose or Tween | 1.875 | 0.1 | No | 50 | 0 | 0 | 0 |
| 18.75 | 1.875 | 0.1 | Dispersed | 100 | 100 | 100 | 0 |
| 18.75 | 1.875 | 0.1 | No | 100 | 100 | 100 | 0 |
| 9.4 | 0.94 | 0.1 | Dispersed | 100 | 0 | 0 | 0 |
| 9.4 | 0.94 | 0.1 | No | 0 | 0 | 0 | 0 |
| 4.7 | 0.47 | 0.1 | Dispersed | 0 | 0 | 0 | 0 |
| 4.7 | 0.47 | 0.1 | No | 0 | 0 | 0 | 0 |

Example 11

Previously manufactured lyophylized mixtures of fibrinogen & thrombin (lot # 012408) were placed into a grinder (Krups) and ground (5 seconds) into a powder. The powdered dressings were placed into a 50 ml conical centrifuge tube. Twenty-five grams of sucrose was ground into powder and placed into another 50 ml conical centrifuge tube. Table 11.1 shows the design of the experiment.

TABLE 11.1

Experimental Design

| Fibrinogen Dose (mg/cm$^2$) | Thrombin Dose (U/cm$^2$) | T:F (U/mg) | Support material and placement | Disk Modification | Weight of Dressing Powder (g) | Weight of Sucrose (g) |
|---|---|---|---|---|---|---|
| 26 | 1.3 | 0.05 | Yes/Dispersed | Hole in center of Disk | 0.416 | 0.584 |
| 26 | 1.3 | 0.05 | Yes/Dispersed | 12.5% Removed as a pie shaped wedge | 0.416 | 0.584 |

For each group 0.1 g of the powder/sucrose was weighed and placed into a Carver 13 mm Evacuable Pellet Die. Seventy-five mg of shredded support material (Dexon™ mesh) was added to the powder and mixed for 5 seconds with a pipette tip. Once the die was filled with the appropriate material, it was placed in a Carver 4350 manual pellet press. Pressure was applied to give an applied load of 1000 lbs. Once the pellets were removed from the die a small hole was placed in the center of two of pellets using a 1/64" drill bit. The other two pellets had 1/8" of the pellet removed in a wedge-shaped piece with the vertex at the center of the pellet. The resulting pellets were removed and placed into a desiccator until tested.

The performance of the test articles was determined using the EVPCA assay as described in Example 2 above. With a modification that a 22 gauge wire was placed into the artery hole and the test article was slid down the wire to come in contact with the artery hole. Once the test article was delivered to the hole the wire was removed and the test proceeded as described. The results are shown in Table 11.2 below.

Results:

TABLE 11.2

| Fibrinogen Dose (mg/cm$^2$) | Support Material Placement | Disk Modification | % Reaching 100 mmHg | % Reaching 150 mmHg | % Reaching 200 mmHg | % Reaching 250 mmHg |
|---|---|---|---|---|---|---|
| 26 | Dispersed | Hole in center of Disk | 50 | 50 | 50 | 50 |
| 26 | Dispersed | 12.5% Removed as a pie shaped wedge | 50 | 0 | 0 | 0 |

Example 12

Enzyme Research Laboratories (ERL) Fibrinogen lot 3170P was formulated in 100 mM Sodium Chloride, 1.1 mM Calcium Chloride, 10 mM Tris, 10 mM Sodium Citrate, and 1.5% Sucrose (Fibrinogen complete buffer). In addition, Human Serum Albumin was added to 80 mg/g of total protein and Tween 80 (non-animal source) was added to 15 mg/g total protein. The final pH of the fibrinogen was 7.4+/−0.1. The fibrinogen concentration was adjusted to 37.5 mg/mL. Once prepared the fibrinogen was placed on ice until use. Thrombin was formulated in 150 mM Sodium Chloride, 40 mM Calcium Chloride, 10 mM Tris and 100 mM L-Lysine. The final pH of the thrombin was 7.4±/−0.1. The thrombin was adjusted to deliver 0.1 units/mg of Fibrinogen or 25 Units/ml thrombin. Once prepared the thrombin was placed on ice until use. The temperature of the fibrinogen and thrombin prior to dispensing was 4° C.+/−2° C.

Cylindrical molds made of 3 mL polypropylene syringes (Becton Dickinson) with the luer-lock end removed were used. The plungers were withdrawn to the 1.0 ml mark.

Cylindrical molds were placed on dry ice. There were two groups of cylindrical molds prepared with one cylindrical mold per group. One group did not have any support material, and the second group contained shredded support material (0.1 gm Dexon™ mesh) dispersed within it. A repeat pipetor was filled with fibrinogen and second repeat pipetor was filled with thrombin. Simultaneously 0.5 ml of fibrinogen and 75 micro liters of thrombin were dispensed into each cylindrical mold. Once each cylindrical mold was filled, they were transferred to a −80° C. freezer until tested. Table 12.1 shows the experimental design.

TABLE 12.1

| Fibrinogen Dose (mg) | Thrombin (Units) | T:F (U/mg) | Support Material |
|---|---|---|---|
| 18.75 | 1.875 | 0.1 | Dispersed |
| 18.75 | 1.875 | 0.1 | No |

The performance of the test articles was determined using a modified EVPCA assay. The EVPCA assay (described in Example 2 above) was modified to further enhance the faithfulness of the assay to the actual conditions that may be encountered in vivo. As described in Example 3, the surrounding of the test blood vessel by closely fitting material can replicate the use of these inventions in sealing an injury deep inside tissue. To further enhance this replication of such a clinical setting, tissue was substituted for the plastic foam that was wrapped around the vessel. The tissue may be chosen to best replicate the intended anatomical location. In this Example commercial meat was used to simulate the leg muscle of a patient undergoing a vascular access procedure. Sufficient tissue was used to simulate a depth of several inches of muscle tissue. Other than this modification, and the employment of an application device as described in Example #3, the assay was carried out as described in Example #2. The results are shown in table 12.2

TABLE 12.2

| Fibrinogen Dose (mg) | Thrombin (Units) | T:F U/mg | Support Material | % Reaching 100 mmHg | % Reaching 150 mmHg | % Reaching 200 mmHg | % Reaching 250 mmHg |
|---|---|---|---|---|---|---|---|
| 18.75 | 1.875 | 0.1 | Dispersed | 100 | 100 | 50 | 0 |
| 18.75 | 1.875 | 0.1 | No | 0 | 0 | 0 | 0 |

What is claimed is:

1. A method for treating wounded internal tissue in a mammal comprising applying to wounded internal tissue for a time sufficient to join or approximate said wounded tissue and/or to reduce the flow of fluid from said wounded tissue at least one haemostatically effective amount of a casted haemostatic material, wherein said casted haemostatic material consists essentially of a substantially homogenous mixture of a fibrinogen component and a fibrinogen activator, wherein said fibrinogen component is present in an amount between 26 to about 450 mg per square centimeter of the surface intended to contact the wounded internal tissue being treated and wherein the fibrinogen activator is employed between about 0.0087-1.000 mg fibrinogen component, and wherein said fibrinogen component and fibrinogen activator are cooled to about 4° C.+/−2° C. before casting.

2. The method of claim 1, wherein said haemostatic material includes at least one support layer.

3. The method of claim 2, wherein said support layer comprises a backing material.

4. The method of claim 2, wherein said support layer comprises an internal support material.

5. The method of claim 2, wherein said support layer comprises a resorbable material.

6. The method of claim 2, wherein said support layer comprises a non-resorbable material.

7. The method of claim 6, wherein said non-resorbable material is selected from the group consisting of silicone polymers, paper, gauze, plastics, non-resorbable suture materials, latexes and suitable derivatives of thereof.

8. The method of claim 2, further comprising at least one physiologically acceptable adhesive between said haemostatic material and said backing layer.

9. The method of claim 5, wherein said resorbable material is selected from the group consisting of proteinaceous materials, carbohydrate substances and resorbable suture materials.

10. The method of claim 9, wherein said proteinaceous material is at least one substance selected from the group consisting of keratin, silk, fibrin, collagen, and gelatin.

11. The method of claim 9, wherein said carbohydrate substance is selected from the group consisting of alginic acid and salts thereof, chitin, chitosan, cellulose, n-acetyl glucosamine, proteoglycans, glycolic acid polymers, lactic acid polymers, glycolic acid/lactic acid co-polymers, and mixtures of two or more thereof.

12. The method of claim 1, wherein said haemostatic material also contains a fibrin crosslinker and/or a source of calcium ions.

13. The method of claim 1, wherein said haemostatic material also contains one or more of the following: at least one filler; at least one solubilizing agent; at least one foaming agent; and at least one release agent.

14. The method of claim 13, wherein said filler is selected from the group consisting of sucrose, lactose, maltose, keratin, silk, fibrin, collagen, gelatin, albumin, polysorbate, chitin, chitosan., alginic acid and salts thereof, cellulose, proteoglycans, glycolic acid polymers, lactic acid polymers, glycolic acid/lactic acid co-polymers, and mixtures of two or more thereof.

15. The method of claim 13, wherein said solubilizing agent is selected from the group consisting of sucrose, lactose, maltose, dextrose, mannose, trehalose, mannitol, sorbitol, albumin, sorbate, polysorbate, and mixtures of two or more thereof.

16. The method of claim 13, wherein said release agent is selected from the group consisting of gelatin, mannitol, sorbitol, polysorbate, sorbitan, lactose, maltose, trehalose, sorbate, glucose and mixtures of two or more thereof.

17. The method of claim 13, wherein said foaming agent is selected from the group consisting of mixtures of sodium bicarbonate/citric acid, sodium bicarbonate/acetic acid, calcium carbonate/citric acid and calcium carbonate/acetic acid.

18. The method of claim 1, wherein said haemostatic material also contains at least one therapeutic supplement selected from the group consisting of antibiotics, anticoagulants, steroids, cardiovascular drugs, growth factors, antibodies (poly and mono), chemoattractants, anesthetics, antiproliferatives/antitumor agents, antivirals, cytokines, colony stimulating factors, antifungals, antiparasitics, antiinflammatories, antiseptics, hormones, vitamins, glycoproteins, fibronectin, peptides, proteins, carbohydrates, proteoglycans, antiangiogenins, antigens, nucleotides, lipids, liposomes, fibrinolysis inhibitors, procoagulants, anticoagulants, vascular constrictors and gene therapy reagents.

* * * * *